US007304203B2

(12) United States Patent
Spelsberg et al.

(10) Patent No.: US 7,304,203 B2
(45) Date of Patent: Dec. 4, 2007

(54) TRANSGENIC TIEG NON-HUMAN ANIMALS

(75) Inventors: Thomas C. Spelsberg, Rochester, MN (US); Malayannan Subramaniam, Zumbrota, MN (US); Merry Jo Velasquez, Cannon Falls, MN (US); Nalini M. Rajamannan, Chicago, IL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/944,454

(22) Filed: Sep. 17, 2004

(65) Prior Publication Data

US 2006/0048238 A1 Mar. 2, 2006

Related U.S. Application Data

(60) Provisional application No. 60/503,996, filed on Sep. 18, 2003.

(51) Int. Cl.
*A01K 67/033* (2006.01)
*A01K 67/027* (2006.01)
*A01K 67/00* (2006.01)

(52) U.S. Cl. .............................. 800/18; 800/13; 800/14
(58) Field of Classification Search ...................... None
See application file for complete search history.

(56) References Cited

U.S. PATENT DOCUMENTS

| 3,687,808 | A | | 8/1972 | Merigan, Jr. et al. |
| 4,415,732 | A | | 11/1983 | Caruthers et al. |
| 4,458,066 | A | | 7/1984 | Caruthers et al. |
| 4,469,863 | A | | 9/1984 | Ts'o et al. |
| 4,959,317 | A | | 9/1990 | Sauer |
| 5,214,136 | A | | 5/1993 | Lin et al. |
| 5,218,105 | A | | 6/1993 | Cook et al. |
| 5,235,033 | A | | 8/1993 | Summerton et al. |
| 5,464,764 | A | * | 11/1995 | Capecchi et al. ............... 435/6 |
| 5,596,086 | A | | 1/1997 | Matteucci et al. |
| 5,750,666 | A | | 5/1998 | Caruthers et al. |
| 5,889,136 | A | | 3/1999 | Scaringe et al. |

OTHER PUBLICATIONS

Fautsch., et al., Characterization of the mouse TGFbeta-inducible early gene (TIEG): conservation of exon and transcriptional regulatory sequences with evidence of additional transcripts. Mamm Genome. Oct. 9, 1998(10):838-42.*
Fautsch et al., GFβ-Inducible Early Gene (TIEG) Also Codes for Early Growth Response α (EGRα): Evidence of Multiple Transcripts from Alternate Promoter. Genomics 51, 1998, pp. 408-416.*
Subramaniam et al., TIEG1 Null Mouse-Derived Osteoblasts Are Defective in Mineralization and in Support of Osteoclast Differentiation in VitroMolecular and Cellular Biology, Feb. 2005, p. 1191-1199, vol. 25, No. 3.*

Reinholz et al., 2004. Differential gene expression of TGFβ inducible early gene (TIEG), Smad 7, Smad 2, and Bard 1 in normal and malignant breast tissue. Breast Cancer Res. Treatment 166:75-88.*
Gerlai R. Gene-targeting studies of mammalian behavior: is it the mutation or the background genotype? Trends Neurosci. May 1996;19(5):177-81.*
Capecchi MR. Altering the genome by homologous recombination. Science. Jun. 16, 1989;244(4910):1288-92. Review.*
Holschneider DP, Shih JC. Genotype to phenotype: challenges and opportunities. Int J Dev Neurosci. Oct. 2000;18(6):615-8.*
Leonard WJ, Shores EW, Love PE. Role of the common cytokine receptor gamma chain in cytokine signaling and lymphoid development. Immunol Rev. Dec. 1995;148:97-114.*
Griffiths I, et al., Current concepts of PLP and its role in the nervous system. Microsc Res Tech. Jun 1, 1998;41(5):344-58.*
Crabbe JC, Wahlsten D, Dudek BC.Genetics of mouse behavior: interactions with laboratory environment. Jun. 4, 1999;284(5420):1670-2.*
Rajamannan NM et al., J Cell Biochem. Feb. 1, 2007;100(2):315-25.TGFbeta inducible early gene-1 (TIEG1) and cardiac hypertrophy: Discovery and characterization of a novel signaling pathway.*
Capecchi, "Targeted Gene Replacement. Researchers can now create mice bearing any chosen mutations in any known gene. The technology is revolutionizing the study of mammalian biology," *Scientific American*, 1994, 270(3):34-41.
Mansour et al., "Mice homozygous for a targeted disruption of the proto-oncogene *int-2* have developmental defects in the tail and inner ear," *Development*, 1993, 117:13-28.
GenBank Accession No. AF049879 dated Nov. 17, 1998.
GenBank Accession No. AF049880 dated Nov. 17, 1998.
GenBank Accession No. AF050110 dated Sep. 3, 1998.
GenBank Accession No. U21847 dated Jan. 16, 1996.
Arad et al., "Phenotypic diversity in hypertrophic cardiomyopathy," *Human Molecular Genetics*, 2002, 11(20):2499-2506.
Bender et al., "TIEG1 Facilitates Transforming Growth Factor-β-Mediated Apoptosis in the Oligodendroglial Cell Line OLI-neu," *J. Neuroscience Research*, 2004, 75:344-352.
Blok et al., "Characterization of an Early Growth Response Gene, Which Encodes a Zinc Finger Transcription Factor, Potentially Involved in Cell Cycle Regulation," *Molecular Endocrinology*, 1995, 9:1610-1620.
Burel et al., "Dichotomy of AML1-ETO Functions: Growth Arrest versus Block of Differentiation," *Molecular and Cellular Biology*, 2001, 21(16):5577-5590.
Chalaux et al., "A zinc-finger transcription factor induced by TGF-β promotes apoptotic cell death in epithelial Mv1Lu cells," *FEBS Letters*, 1999, 457:478-482.

(Continued)

*Primary Examiner*—Joseph Woitach
*Assistant Examiner*—Maria Leavit
(74) *Attorney, Agent, or Firm*—Fish & Richardson P.C.

(57) ABSTRACT

Materials and methods related to a transgenic non-human animal (e.g., a transgenic non-human mammal) whose genome comprises a disrupted TIEG allele are provided. Methods for making such transgenic non-human animals, and using them to identify and characterize agents that affect conditions related to TIEG activity, such as cardiac hypertrophy and bone formation also are provided. In addition, materials and methods related to the treatment of hypertrophic cardiomyopathy are provided.

9 Claims, 14 Drawing Sheets

OTHER PUBLICATIONS

Cibelli et al., "Cloned Transgenic Calves Produced from Nonquiescent Fetal Fibroblasts," *Science*, 1998, 280:1256-1258.

Dennler et al., "Direct binding of Smad3 and Smad4 to critical TGFβ-inducible elements in the promoter of human plasminogen activator inhibitor-type 1 gene," *The EMBO J.*, 1998, 17(11):3091-3100.

Geisterfer-Lowrance et al., "A Mouse Model of Familial Hypertrophic Cardiomyopathy," *Science*, 1996, 272:731-734.

Gingery et al., "Phosphatidylinositol 3-Kinase Coordinately Activates the MEK/ERK and AKT/NFκB Pathways to Maintain Osteoclast Survival," *J. Cell. Biochem.*, 2003, 89:165-179.

Guatelli et al., "Isothermal, in vitro amplification of nucleic acids by a multienzyme reaction modeled after retroviral replication," *Proc. Natl. Acad. Sci. USA*, 1990, 87:1874-1878.

Heaney and Melmed, "Pituitary tumour transforming gene: a novel factor in pituitary tumour formation," *Baillière's Clinical Endocrinology and Metabolism*, 1999, 13(3):367-380.

Hyrup and Nielssen, "Peptide Nucleic acids (PNA): Synthesis, Properties and Potential Applications," *Bioorgan. Med. Chem.*, 1996, 4(1):5-23.

James et al., "Transgenic Modeling of a Cardiac Troponin I Mutation Linked to Familiar Hypertrophic Cardiomyopathy," *Circ. Res.*, 2000, 87:805-811.

Johnsen et al., "Modulation of Transforming Growth Factor β (TGFβ)/Smad Transcriptional Responses through Targeted Degradation of TGFβ-inducible Early Gene-1 by Human Seen in Absentia Homologue," *J. Biol. Chem.*, 2002, 277(34):30754-30759.

Johnsen et al., "Transcriptional Regulation of Smad2 is Required for Enhancement of TGFβ/Smad Signaling by TGFβ Inducible Early Gene," *J. Cell. Biochem.*, 2002, 87:233-241.

Johnsen et al., "TGFβ Inducible early gene enhances TGFβ/Smad-dependent transcriptional responses," *Oncogene*, 2002, 21:5783-5790.

Kakar, "Molecular cloning, genomic organization, and identification of the promoter for the human pituitary tumor transforming gene (PTTG)," *Gene*, 1999, 240:317-324.

Koli and Arteaga, "Complex Role of Tumor Cell Transforming Growth Factor (TGF)-βs on Breast Carcinoma Progression," *J. Mammary Gland Biology and Neoplasia*, 1996, 1(4):373-380.

Kook et al., "Cardiac hypertrophy and histone deacetylase-dependent transcriptional repression mediated by the atypical homeodomain protein Hop," *J. Clin Invest.*, 2003, 112:863-871.

Lewis, "PCR's Competitors Are Alive and Well and Moving Rapidly Towards Commercialization," *Genetic Engineering News*, 1992, 12(9):1-3.

Lin et al., "Control of Mouse Cardiac Morphogenesis and Myogenesis by Transcription Factor MEF2C," *Science*, 1997, 276:1404-1407.

Marian et al., "A transgenic rabbit model for human hypertrophic cardiomyopathy," *J. Clin. Invest.*, 1999, 104:1683-1692.

Maron et al., "Hypertrophic Cardiomyopathy. Interrelations of Clinical Manifestations, Pathophysiology, and Therapy (First of Two Parts)," *New Engl. J. Med.*, 1987, 316(13):780-789.

Maron et al., "Hypertrophic Cardiomyopathy. Interrelations of Clinical Manifestations, Pathophysiology, and Therapy (Second of Two Parts)," *New Engl. J. Med.*, 1987, 316(14):844-852.

Miyamoto et al., "A Dominant-negative Mutant of Androgen Receptor Coregulator ARA54 Inhibits Androgen Receptor-mediated Prostate Cancer Growth," *J. Biol. Chem.*, 2002, 277(7):4609-4617.

Molkentin et al., "A Calcineurin-Dependent Transcriptional Pathway for Cardiac Hypertrophy," *Cell*, 1998, 93:215-228.

Moustakas et al., "Mechanisms of TGF-β signaling in regulation of cell growth and differentiation," *Immunology Letters*, 2002, 82:85-91.

Moustakas and Kardassis, "Regulation of the human p21/WAF1/Cip1 promoter in hepatic cells by functional interactions between Sp1 and Smad family members," *Proc. Natl. Acad. Sci. USA*, 1998, 95:6733-6738.

Noti et al., "The Zinc Finger Transcription Factor Transforming Growth Factor β-Inducible Early Gene-1 Confers Myeloid-specific Activation of the Leukocyte Integrin *CD11d* Promoter," *J. Biol. Chem.*, 2004, 279(26):26948-26958.

Oberst et al., "Dominant-negative Effect of a Mutant Cardiac Troponin T on Cardiac Structure and Function in Transgenic Mice," *J. Clin. Invest.*, 1998, 102:1498-1505.

Orban et al., "Tissue- and site-specific DNA recombination in transgenic mice," *Proc. Natl. Acad. Sci. USA*, 1992, 89:6861-6865.

Pei, "Genomic Organization and Identification of an Enhancer Element Containing Binding Sites for Multiple Proteins in Rat Pituitary Tumor-transforming Gene," *J. Biol. Chem.*, 1998, 273(9):5219-5225.

Pei and Melmed, "Isolation and Characterization of a Pituitary Tumor-Transforming Gene (PTTG)," *Molecular Endocrinology*, 1997, 11:433-441.

Ramos-Morales et al., "Cell cycle regulated expression and phosphorylation of *hpttg* proto-oncogene product," *Oncogene*, 2000, 19:403-409.

Rickard et al., "Phytoestrogen Genistein Acts as an Estrogen Agonist on Human Osteoblastic Cells Through Estrogen Receptors α and β," *J. Cell. Biochem.*, 2003, 89:633-646.

Sambrook et al., "Analysis and Cloning of Eukaryotic Genomic DNA," *Molecular Cloning: A Laboratory Manual*, Second Edition, 1989, Cold Spring Harbor Press, Plainview, NY, Sections 9.37-9.52.

Sambrook et al., "Analysis of Recombinant DNA Clones-Southern Transfer," *Molecular Cloning: A Laboratory Manual*, 1982, pp. 382-389.

Seidman and Seidman, "The Genetic Basis for Cardiomyopathy: from Mutation Identification to Mechanistic Paradigms," *Cell*, 2001, 104:557-567.

Shastry, "Gene disruption in mice: Models of development and disease," *Mol. Cell. Biochem.*, 1998, 181:163-179.

Subramaniam et al., "Tissue, Cell Type, and Breast Cancer Stage-Specific Expression of a TGF-β Inducible Early Transcription Factor Gene," *J. Cell. Biochem.*, 1998, 68:226-236.

Subramaniam et al., "Identification of a novel TGF-β-regulated gene encoding a putative zinc finger protein in human osteoblasts," *Nucl. Acids Res.*, 1995, 23(23):4907-4912.

Subramaniam et al., "Osteoblast and Osteoclast Isolated and Cultured In Vitro From Wild Type and TIEG Nu. Mice Show Defects in Differentiation," *ASBMR 25th Annual Meeting*, Sep. 19-23, 2003, Minneapolis, MN, p. S5, Abstract No. 1013.

Summerton and Weller, "Morpholino Antisense Oligomers: Design, Preparation, and Properties," *Antisense Nucleic Acid Drug Dev.*, 1997, 7:187-195.

Tardiff et al., "A Truncated Cardiac Troponin T Molecule in Transgenic Mice Suggests Multiple Cellular Mechanisms for Familial Hypertrophic Cardiomyopathy," *J. Clin. Invest.*, 1998, 101:2800-2811.

Vega et al., "Dual roles of modulatory calcineurin-interacting protein 1 in cardiac hypertrophy," *Proc. Natl. Acad. Sci. USA*, 2003, 100(3):669-674.

Vikstrom and Leinwand, "Contractile protein mutations and heart disease," *Current Opinion in Cell Biology*, 1996, 8:97-105.

Vikstrom et al., "A murine model for hypertrophic cardiomyopathy," *Z. Kardiol.*, 1995, 84(Suppl. 4):49-54, including English-language Summary.

Wakayama et al., "Full-term development of mice from enucleated oocytes injected with cumulus cell nuclei," *Nature*, 1998, 394:369-374.

Weiss, "Hot Prospect for New Gene Amplifier," *Science*, 1991, 254:1292-1293.

Wilmut et al., "Viable offspring derived from fetal and adult mammalian cells," *Nature*, 1997, 385:810-813.

Yang et al., "A Mouse Model of Myosin Binding Protein C Human Familial Hypertrophic Cardiomyopathy," *J. Clin. Invest.*, 1998, 102:1292-1300.

Zhang et al., "Association of Class II Histone Deacetylases with Heterochromatin Protein 1: Potential Role for Histone Methylation in Control of Muscle Differentiation," *Mol. Cell. Biol.*, 2002, 22(20):7302-7312.

Zhou and Olson, "Dimerization through the Helix-Loop-Helix Motif Enhances Phosphorylation of the Transcription Activation Domains of Myogenin," *Mol. Cell. Biol.*, 1994, 14(9):6232-6243.

\* cited by examiner

Loss of TIEG Causes Differentiation Defects in Both Precursors and Support Cells TIEG KO Reduces the RANKL / OPG Ratio

TRANSGENIC TIEG NON-HUMAN ANIMALS

CROSS REFERENCE TO RELATED APPLICATIONS

This application claims priority under 35 U.S.C. §119(e) of U.S. Application No. 60/503,996, filed Sep. 18, 2003.

STATEMENT AS TO FEDERALLY SPONSORED RESEARCH

Funding for the work described herein was provided in part by the federal government, National Institutes of Health Grant number DE 14036. The federal government may have certain rights in the invention.

BACKGROUND

1. Technical Field

The invention involves methods and materials related to making and using transgenic non-human animals with genomic disruptions affecting the expression of a transforming growth factor β-inducible early gene. The invention also relates to heart conditions and methods for treating heart conditions.

2. Background Information

TGFβ and members of its signaling pathway are tumor suppressors that regulate many diverse tissue and cell processes, including differentiation, apoptosis, and cell proliferation. For example, TGFβ inhibits proliferation, induces cell differentiation and apoptosis, and alters gene expression in different cell types. TGFβ-inducible early gene (TIEG) encodes a protein that is rapidly induced (as is its mRNA) by all three isoforms of TGFβ. TIEG protein is 480 amino acids in length (72 kDa) and contains a zinc finger region that has homology with the 3-zinc finger family of transcription factors (e.g., Sp-1, BTEB, EGR-1, and the Krüppel-like factors). The TIEG gene is localized on chromosome 8q22.2. TIEG protein has been identified in many human tissues and cell types, including cells in the breast, uterus, brain, pancreas, muscle, and bone. TIEG plays a role in TGFβ-induced inhibition of cell proliferation and apoptosis in human osteoblast cells, pancreatic carcinoma cells, and epithelial and liver cancer cells.

SUMMARY

The invention is based, in part, on the discovery that transgenic non-human mammals whose genomes contain a disruption in a nucleic acid encoding TIEG, develop cardiac hypertrophy during the aging process. Such non-human mammals also have defects in osteoblast and osteoclast differentiation and function, which can lead to defects in bone formation. In addition, transgenic non-human mammals whose genomes contain a disruption in a nucleic acid encoding TIEG can exhibit connective tissue defects. As a result, such transgenic mice provide a model to study the biological role of TIEG in diverse biological systems.

In general, one aspect of the invention features a transgenic rodent whose genome includes a disruption of an endogenous TIEG nucleic acid and progeny and cells of the rodent. The transgenic rodent can be a mouse and can have a genetic background selected from the group consisting of B6, 129Sv/J, and FVB. The disruption can be heterozygous or homozygous. Osteoblasts or osteoclasts from the rodent can have a decreased ability to differentiate in vitro relative to osteoblasts or osteoclasts from a corresponding control rodent. The disruption can result from deletion of a portion of the endogenous TIEG gene (e.g., deletion of exons 1 and 2). The transgenic rodent can develop cardiac hypertrophy. The rodent can be a male rodent. The rodent can exhibit a symptom of human hypertrophic cardiomyopathy.

In another embodiment, the invention features a progeny of the transgenic rodent.

In another embodiment, the invention features cells isolated from the transgenic rodent. The cells can be cardiomyocytes, osteoblasts, or osteoclasts.

In another aspect, the invention features a nucleic acid construct that includes a disrupted TIEG nucleic acid, wherein the disruption prevents the expression of a functional TIEG polypeptide from the nucleic acid.

Another aspect of the invention features a method for determining whether or not a test compound is a potential treatment compound for human hypertrophic cardiomyopathy. The method includes (a) administering the test compound to a male TIEG −/− mouse, and (b) determining whether or not the mouse develops symptoms of human hypertrophic cardiomyopathy to a lesser degree than those developed in a control male TIEG −/− mouse not receiving the test compound, wherein a lesser degree of symptoms of human hypertrophic cardiomyopathy in the mouse indicates that the test compound is a potential treatment compound for human hypertrophic cardiomyopathy. The test compound can be an siRNA or antisense oligo that reduces the expression of a PTTG-1 polypeptide.

Another aspect of the invention features a method for treating hypertrophic cardiomyopathy in a mammal. The method includes administering a TIEG polypeptide, nucleic acid encoding the TIEG polypeptide, or an activator of TIEG polypeptide activity to the mammal under conditions wherein the severity of a symptom of hypertrophic cardiomyopathy is reduced in the mammal. The mammal can be a human. The TIEG polypeptide can be administered to the mammal. The activator of TIEG polypeptide activity can be administered to the mammal. Activators of TIEG polypeptide activity can include, without limitation, TGFβ, EGF, BMP-2, BMP-6, or estrogen.

Another aspect of the invention features a method for treating hypertrophic cardiomyopathy in a mammal. The method includes administering a molecule to the mammal under conditions wherein the severity of a symptom of hypertrophic cardiomyopathy is reduced in the mammal, wherein the molecule reduces expression of a PTTG-1 polypeptide in the mammal or inhibits a PTTG-1 polypeptide activity in the mammal. The mammal can be a human. The molecule can be an siRNA or antisense oligo that reduces the expression of a PTTG-1 polypeptide. The molecule can reduce a PTTG-1 polypeptide activity. The molecule can be TGFβ, EGF, BMP-2, BMP-6, or estrogen.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
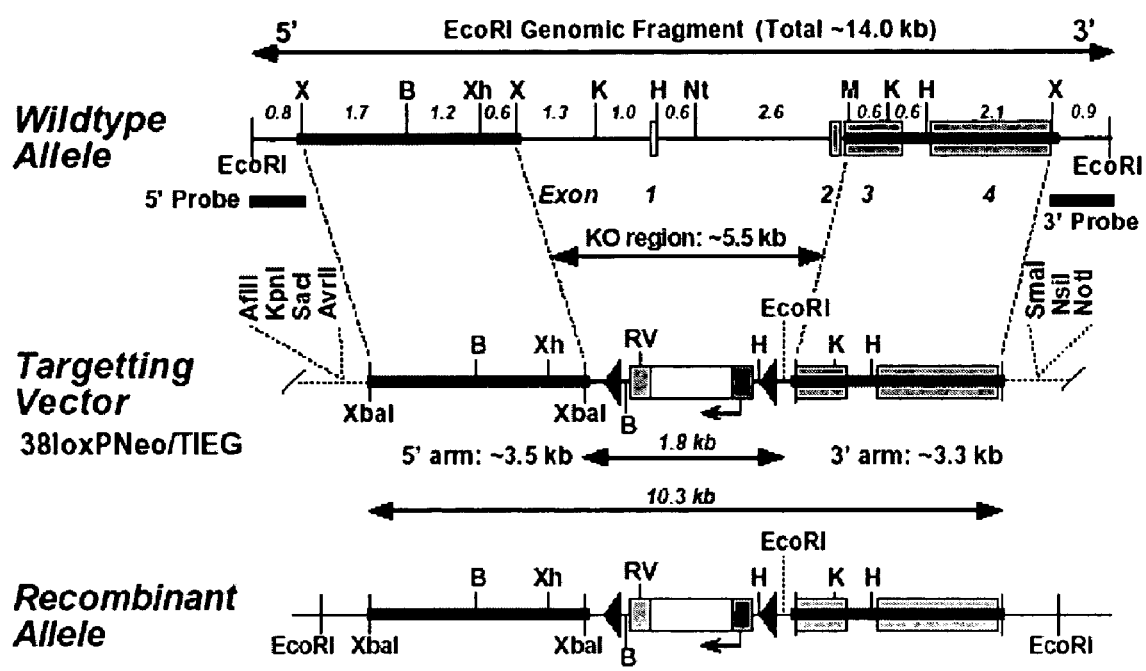
FIG. 1 is a schematic representation of the wild-type allele of the TIEG gene, the targeting vector, and the recombinant allele.

In general, the invention provides a transgenic non-human animal whose genome contains a disruption in the endogenous TIEG nucleic acid. Such transgenic non-human animals develop cardiac hypertrophy (e.g., concentric left ventricular hypertrophy) as they age. In particular, transgenic non-human animals of the invention have an increase in cardiac myocyte cell number and a decrease in cardiac myocyte cell size and as such, it appears that there is an increase in cardiac myocyte differentiation after the mice are born. In addition, osteoblasts and osteoclasts from such transgenic non-human animals exhibit defects in differentiation. Further, transgenic non-human animals containing a disruption in the endogenous TIEG nucleic acid exhibit connective tissue defects (e.g., less tendon strength than that exhibited in tendons from control animals). The transgenic animals (e.g., transgenic mice) of the invention are valuable models for studying the role of TIEG in bone formation, cardiac myocyte differentiation, cell proliferation, cancer, and connective tissue. In one embodiment, the male transgenic non-human animals provided herein can be used as a model to study hypertrophic cardiomyopathy (HCM) since male transgenic non-human animals containing a disruption in the endogenous TIEG nucleic acid develop, with age and in a non-stress induced manner, the three hallmark symptoms of human HCM: unexplained hypertrophy, myocyte disarray, and fibrosis.

Production of TIEG Deficient Animals

The invention features non-human mammals including a disrupted TIEG allele, and progeny and cells of such animals. Disruption of the TIEG gene results in non-human mammals with reduced levels of TIEG when compared with a corresponding wild-type animal. TIEG deficient animals can be referred to as "knockout animals." Non-human mammals include, for example, rodents such as rats, guinea pigs, and mice, farm animals such as pigs, sheep, goats, horses, and cattle, and non-human primates (e.g., baboons, squirrel monkeys and chimpanzees). TIEG deficient mice are particularly useful. Cells and cell lines deficient in TIEG can be derived from TIEG knockout animals, using known techniques. Such animals may be used to derive a cell line that may be used in culture, either a primary culture or for continuous culture.

Nucleic acid constructs useful for producing knockout animals include a disrupted TIEG nucleic acid. As used herein, "disrupted TIEG nucleic acid" refers to a modification in the TIEG nucleic acid such that the expression of a functional TIEG polypeptide is reduced or prevented. Modifications that can result in a disrupted TIEG nucleic acid include, without limitation, insertions, deletions, substitutions, and combinations thereof. Modifications can be made in any region of a TIEG allele, including, an intron, exon, promoter, or 5'- or 3'-untranslated regions, and combinations thereof. Suitable exons can include any of the four exons (e.g., exons 1 and 2) of the TIEG nucleic acid. For example, a stop codon can be introduced into a TIEG nucleic acid or a selectable marker can be substituted for a region of the TIEG gene such that expression of a functional TIEG polypeptide is reduced or prevented. See, Shastry, B. S., *Mol. Cell Biochem.*, 181(1-2):163-179, 1998, for a review of gene targeting technology.

Typically, TIEG genomic sequences are used in the nucleic acid construct. Genomic sequences can be isolated using known molecular techniques and human or mouse nucleotide sequences as probes and/or as PCR primers. The genomic nucleic acid sequence of TIEG also can be found in GenBank under Accession No. AF049879, AF049880, and AF050110. A human TIEG cDNA and human TIEG amino acid sequence can be found in GenBank Accession No. U21847.

A nucleic acid sequence encoding a selectable marker generally is used to interrupt the targeted site by homologous recombination. Typically, the nucleic acid encoding the selectable marker is flanked by sequences homologous to the sequences flanking the desired insertion site. It is not necessary for the flanking sequences to be immediately adjacent to the desired insertion site. Suitable nucleic acids encoding selectable markers for positive drug selection include, for example, the aminoglycoside 3' phosphotransferase gene, which encodes a gene product that imparts resistance to geneticin (G418, an aminoglycoside antibiotic), and the hygromycin-B-phosphotransferase gene, which encodes a gene product that imparts hygromycin resistance. Other selection systems include nucleic acids encoding negative-selection markers such as the thymidine kinase (TK) gene from herpes simplex. Constructs utilizing both positive and negative selection also can be used. For example, a construct can contain the aminoglycoside phosphotransferase gene and the TK gene. In this system, cells are selected that are resistant to G418 and sensitive to gancyclovir. Any selectable marker suitable for inclusion in a knockout vector is within the scope of the present invention.

Suitable nucleic acid constructs are amenable to genomic integration by homologous recombination. Non-limiting examples of such constructs include pKO Scrambler, pMC1neo, and pMC1-hsv-tk, all from Stratagene (La Jolla, Calif.).

In addition, Cre/lox technology can be used to generate transgenic non-human mammals with conditional TIEG gene deletions. See, Orban, P. C., et al., *Proc. Natl. Acad. Sci. USA*, (1992) 89 (15): 6861-6865, and U.S. Pat. No. 4,959,317 for a review of Cre/lox technology.

To create animals having a particular gene inactivated in all cells, it is necessary to introduce a knockout construct into the germ cells (sperm or eggs, i.e., the "germ line") of the desired species. A targeting construct can be introduced into the pronuclei of fertilized eggs by microinjection. Targeting constructs for microinjection can be prepared by any method known in the art. For example, a nucleic acid construct for microinjection can be cleaved with enzymes appropriate for removing the bacterial plasmid sequences, and the resulting DNA fragments gel-purified.

Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking a functional TIEG gene. That is, cultured ES cells can be transformed with a knockout construct and cells selected in which the TIEG gene is disrupted.

Nucleic acid constructs can be introduced into ES cells, for example, by electroporation or other standard technique. A number of techniques can be used to detect or select homologous recombinants. For example, PCR can be used to screen pools of transformant cells for homologous insertion, followed by screening of individual clones. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA (reverse-transcriptase PCR, RT-PCR), including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplified. See, for example, Lewis, R. *Genetic Engineering News*, 12(9):1, 1992; Guatelli et al., *Proc. Natl. Acad. Sci. USA*, 87:1874-1878, 1990; and Weiss, R., *Science*, 254:1292, 1991. Alternatively, positive and/or negative selection techniques, including positive and/or negative drug selection techniques, can be used to identify clones.

The ES cells further can be characterized to determine the number of targeting events. For example, genomic DNA can be harvested from ES cells and used for Southern analysis. See, for example, Section 9.37-9.52 of Sambrook et al., *Molecular Cloning, A Laboratory Manual*, second edition, Cold Spring Harbor Press, Plainview; N.Y., 1989.

To generate a knockout animal, ES cells having at least one inactivated TIEG allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain founder animals, whose cells (including germ cells) carry the inactivated TIEG allele. If the original ES cell was heterozygous for the inactivated TIEG allele, several of these animals can be bred with each other in order to generate animals homozygous for the inactivated allele. Once the founder animals are produced, they may be bred, inbred, outbred, or crossbred to produce colonies of the particular animal (e.g., a B6, 129Sv/J, or FVB mouse).

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with constructs, it is useful to incorporate at least about 7 kb of homologous DNA into the targeting construct. In addition, it is also useful to prepare the constructs from isogenic DNA.

Embryos derived from microinjected eggs can be screened for homologous recombination events in several ways. For example, if the TIEG allele is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate transgenic non-human mammals of the invention. For example, fetal fibroblasts can be genetically modified such that they contain an inactivated endogenous TIEG allele thereby preventing TIEG expression, and then fused with enucleated oocytes. After activation of the oocytes, the eggs are cultured to the blastocyst stage, and implanted into a recipient. See, Cibelli, J. B. et al., *Science*, (1998) 280:1256-1258. Adult somatic cells, including, for example, cumulus cells and mammary cells, can be used to produce animals such as mice and sheep, respectively. See, for example, Wakayama, T. et al., *Nature*, (1998) 394(6691):369-374; and Wilmut, I. et al., *Nature*, (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama, T. et al., 1998, supra. Transgenic non-human mammals heterozygous for a disrupted endogenous TIEG allele can be mated to produce homozygous non-human mammals.

Genotype

A transgenic non-human mammal of the invention can be either heterozygous or homozygous for an inactivated TIEG allele. Initial screening to determine whether a genome comprises a TIEG nucleic acid construct can be accomplished by Southern blot analysis or PCR techniques. See, for example, sections 9.37-9.52 of Sambrook et al., 1989, *Molecular Cloning, A Laboratory Manual*, second edition, Cold Spring Harbor Press, Plainview, N.Y., for a description of Southern analysis. Further, endogenous TIEG mRNA expression levels in tissues from a transgenic non-human mammal can be assessed using techniques that include, but are not limited to, Northern blot analysis of tissue samples obtained from the mammal, in situ hybridization analysis, and RT-PCR. For example, a sample such as tail tissue can be collected from a transgenic mouse whose genome is suspected to include a TIEG nucleic acid construct. Nucleic acid molecules (e.g., DNA) can be purified from the sample using a commercially available kit (e.g., the Qiagen DNeasy Tissue Kit). The purified nucleic acid molecules can be used to genotype the transgenic mouse, e.g., by hybridizing a labeled probe to the nucleic acid molecule and blotting or by amplifying portions of the TIEG nucleic acid construct. Amplified reaction products can be separated by gel electrophoresis, and, based on the presence or absence of genotyping bands, the transgenic mouse can be classified as non-transgenic, heterozygous, or homozygous. Segregation analysis of PCR products can be used to determine heterozygosity or homozygosity.

Phenotype

In addition to exhibiting a particular genotype, a transgenic non-human animal of the invention also can exhibit one or more useful phenotypes. For example, a transgenic non-human animal (e.g., mammal such as a mouse) can develop cardiac hypertrophy or cancer, or have alterations in bone formation and fracture repair. Cells isolated from a transgenic animal of the invention also can have a particular phenotype. For example, as described herein, osteoclasts and osteoblasts isolated from TIEG knockout animals are defective in differentiation. It is understood that the presence of a particular phenotype is assessed by comparing that phenotype to the corresponding phenotype exhibited by a suitable control cell or non-human mammal. Suitable control non-human mammals can include wild-type mammals or mammals heterozygous for a disruption in a TIEG allele.

Using Transgenic Non-Human Animals as Disease Models

The transgenic non-human animals provided herein can be used as models for evaluating the role of TIEG in conditions such as cancer, cardiac hypertrophy, bone loss, osteoporosis, fracture repair, and wound healing. For example, the role of TIEG in cancer can be evaluated by breeding transgenic non-human animals (e.g., a transgenic non-human mammal) of the invention with transgenic non-human animals that are susceptible or prone to developing cancer (e.g., FVB mice). FVB mice are commercially available from Jackson Laboratories and are mildly prone to developing spontaneous breast tumors. In particular, TIEG (−/−) mice can be bred with FVB mice, and transgenic mice deficient in TIEG and having the FVB background can be selected. Such mice may have an increased susceptibility to developing tumors or develop spontaneous tumors at an earlier age.

Transgenic non-human animals (e.g., a transgenic non-human mammal) of the invention can be used to screen, for example, compounds that alter conditions related to TIEG activity, such as cancer (e.g., prostrate, breast, pancreas, or multiple myeloma), bone loss, osteoporosis, and fracture repair. In one embodiment, male TIEG knockout mice, which develop HCM with age and in a non-stress induced manner, are used to identify compounds capable of preventing or reducing the development of HCM. For example, small molecule chemical libraries can be screened for HCM treatment compounds using the male TIEG knockout mice.

As used herein, suitable test compounds include, without limitation, biological macromolecules such as RNA or DNA oligonucleotide (e.g., silencing RNA, antisense oligonucleotides, or ribozymes) or a polypeptide of any length; nucleic acid analogs such as morpholinos or peptide nucleic acids (PNAs); chemical compounds; mixtures of chemical compounds; or extracts isolated from bacterial, plant, fungal, or animal matter. The concentration of the test compound can depend on the type of compound and in vitro test data.

Transgenic non-human animals (e.g., a transgenic non-human mammal) can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Methods of Inducing Proliferation of Cardiac Myocytes

As described herein, transgenic non-human animals that are deficient in TIEG can develop cardiac hypertrophy with age. In such animals, cardiac hypertrophy appears to result from an increase in cell number. This indicates proliferation can be induced in cardiac myocytes by decreasing TIEG levels in cardiac myocytes. TIEG levels can be decreased in cardiac myocytes, either in vitro or in vivo, by reducing expression of TIEG (e.g., with a silencing RNA (siRNA) or by an antisense oligonucleotide) or inhibiting TIEG.

siRNAs can be produced using known technology. See, for example, U.S. Pat. Nos. 5,889,136; 4,415,732; and 4,458,066. In general, two 21-mer RNA oligomers with two deoxythymidines at the 3' terminus and 19 nucleotide complementary sequences can be synthesized then mixed to allow them to hybridize. The duplex can be mixed with a transfection agent and added to cell culture at concentrations of about 100 nM. Symmetric 3' overhangs can aid in the formation of approximately equimolar ratios of sense and antisense target RNA-cleaving siRNAs.

TIEG levels can be reduced by contacting cardiac myocytes with an effective amount of a modulator described above. For example, a modulator can be administered to a mammal such as a human patient that has damaged heart tissue (e.g., from ischemic damage, coronary artery disease, infections, inflammatory conditions, drug toxicity such as chemotherapy drug toxicity, viral induced toxicity, lymphocytic induced toxicity, or cancer induced toxicity). Modulators can be administered by any route, including orally and parenterally. Cells also can be contacted in vitro by adding an effective amount of the modulator to the culture medium. "Effective amount" refers to an amount of a modulator that results in decreased levels of TIEG. Proliferation can be monitored in cells contacted with a modulator using known methods.

Treating Hypertrophic Cardiomyopathy

Hypertrophic cardiomyopathy can be treated or prevented by administering a TIEG polypeptide, a nucleic acid encoding a TIEG polypeptide, or an activator of TIEG polypeptide activity to a mammal. For example, nucleic acid encoding a TIEG polypeptide can be inserted into a vector (e.g., viral vector) that is administered to a hypertrophic cardiomyopathy patient or person suspected to develop hypertrophic cardiomyopathy. Such a vector can be designed to contain a regulatory sequence (e.g., a promoter sequence) that drives TIEG polypeptide expression in heart cells. Expression of TIEG polypeptides can protect mammals from developing symptoms of hypertrophic cardiomyopathy. Any method, including those provided herein, can be used to administer a TIEG polypeptide, a nucleic acid encoding a TIEG polypeptide, or an activator of TIEG polypeptide activity. Examples of activators of TIEG polypeptide activity can include, without limitation, TGFβ, EGF, BMP-2, BMP-6, and estrogen.

Hypertrophic cardiomyopathy can be treated or prevented by reducing PTTG-1 polypeptide activity or expression levels within a mammal. For example, a molecule that reduces PTTG-1 polypeptide expression or PTTG-1 polypeptide activity can be administered to a hypertrophic cardiomyopathy patient or person suspected to develop hypertrophic cardiomyopathy. Such molecules include, without limitation, siRNA molecules, antisense molecules, antigene molecules, TIEG polypeptides, TGFβ polypeptides, EGF polypeptides, BMP-2 polypeptides, BMP-6 polypeptides, and estrogen. The nucleic acid and amino acid sequences for human and mouse PTTG-1 can be found at GenBank® accession numbers: NM_004219, NM_013917, and AF069051. Target sites for siRNA against PTTG-1 can be as follows: 5'-AAGACCTGCAAT-AATC-CAGAA-3' (SEQ ID NO:1); 5'-AATGGCTACTCTGATC-TATGT-3' (SEQ ID NO:2); 5'-AAAGCCTTAGATGG-GAGATCT-3' (SEQ ID NO:3); 5'-AAAGGCTTT-GGGAACTGTCAA-3' (SEQ ID NO:4); 5'-AAGATGACTGAGAAGACTGTT-3' (SEQ ID NO:5);

5'-AATCTGTTGCAGTCTCCTTCA-3' (SEQ ID NO:6); and 5'-AAGCT-CTGTTCCTGCCTC-AGA-3' (SEQ ID NO:7).

Antisense Oligonucleotides

Antisense oligonucleotides can be used to decrease levels of TIEG and/or PTTG protein. The antisense oligonucleotides in accordance with this invention are at least 8 nucleotides in length. For example, a nucleic acid can be about 8, 9, 10-20 (e.g., 11, 12, 13, 14, 15, 16, 17, 18, 19, or 20 nucleotides in length), 15 to 20, 18-25, or 20-50 nucleotides in length. In other embodiments, antisense molecules can be used that are greater than 50 nucleotides in length, including the full-length sequence of a TIEG or PTTG mRNA. As used herein, the term "oligonucleotide" refers to an oligomer or polymer of RNA or DNA or analogs thereof. Nucleic acid analogs can be modified at the base moiety, sugar moiety, or phosphate backbone to improve, for example, stability, hybridization, or solubility of a nucleic acid. Modifications at the base moiety include substitution of deoxyuridine for deoxythymidine, and 5-methyl-2'-deoxycytidine and 5-bromo-2'-deoxycytidine for deoxycytidine. Other examples of nucleotide bases that can be substituted for a natural base include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleotide bases include those disclosed, for example, in U.S. Pat. No. 3,687,808.

Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone. See, for example, U.S. Pat. Nos. 4,469,863, 5,235,033, 5,750,666, and 5,596,086 for methods of preparing oligonucleotides with modified backbones.

Antisense oligonucleotides of the invention also can be modified by chemical linkage to one or more moieties or conjugates that enhance the activity, cellular distribution or cellular uptake of the oligonucleotide. Such moieties include, but are not limited to, lipid moieties (e.g., a cholesterol moiety); cholic acid; a thioether moiety (e.g., hexyl-S-tritylthiol); a thiocholesterol moiety; an aliphatic chain (e.g., dodecandiol or undecyl residues); a phospholipid moiety (e.g., di-hexadecyl-rac-glycerol or triethyl-ammonium 1,2-di-O-hexadecyl-rac-glycero-3-H-phosphonate); a polyamine or a polyethylene glycol chain; adamantane acetic acid; a palmityl moiety; or an octadecylamine or hexylamino-carbonyl-oxycholesterol moiety. The preparation of such oligonucleotide conjugates is disclosed in, for example, U.S. Pat. Nos. 5,218,105 and 5,214,136.

Methods for synthesizing antisense oligonucleotides are known, including solid phase synthesis techniques. Equipment for such synthesis is commercially available from several vendors including, for example, Applied Biosystems (Foster City, Calif.). Alternatively, expression vectors that contain a regulatory element that directs production of an antisense transcript can be used to produce antisense molecules.

Antisense oligonucleotides can bind to a nucleic acid encoding TIEG, including DNA encoding TIEG RNA (including pre-mRNA and mRNA) transcribed from such DNA, and also cDNA derived from such RNA, under physiological conditions (i.e., physiological pH and ionic strength). For example, an antisense oligonucleotide can hybridize under physiological conditions to the nucleotide sequence set forth in GenBank Accession No. U21847. In one embodiment, an antisense or antigene PNA oligo can be used to reduce the level of TIEG polypeptide in a mammal (e.g., human).

It is understood in the art that the sequence of an antisense oligonucleotide need not be 100% complementary to that of its target nucleic acid to be hybridizable under physiological conditions. Antisense oligonucleotides hybridize under physiological conditions when binding of the oligonucleotide to the TIEG or PTTG nucleic acid interferes with the normal function of the TIEG or PTTG nucleic acid, and non-specific binding to non-target sequences is minimal.

Target sites for TIEG and PTTG antisense oligonucleotides include the regions encompassing the translation initiation or termination codon of the open reading frame (ORF) of the gene. In addition, the ORF has been targeted effectively in antisense technology, as have the 5' and 3' untranslated regions. Furthermore, antisense oligonucleotides have been successfully directed at intron regions and intron-exon junction regions. Further criteria can be applied to the design of antisense oligonucleotides. Such criteria are well known in the art, and are widely used, for example, in the design of oligonucleotide primers. These criteria include the lack of predicted secondary structure of a potential antisense oligonucleotide, an appropriate G and C nucleotide content (e.g., approximately 50%), and the absence of sequence motifs such as single nucleotide repeats (e.g., GGGG runs). The effectiveness of antisense oligonucleotides at modulating expression of a TIEG nucleic acid can be evaluated by measuring levels of the TIEG mRNA or protein (e.g., by Northern blotting, RT-PCR, Western blotting, ELISA, or immunohistochemical staining).

The invention will be further described in the following examples, which do not limit the scope of the invention described in the claims.

EXAMPLES

Example 1

Construction of a TIEG Targeting Vector

The murine TIEG gene was cloned from a mouse 129/Sv embryonic stem cell (ES cell) library in P1 phage using a PCR-based screen with primers designed to a conserved region of the mouse and human TIEG cDNAs. The nucleotide and amino acid sequence of human and mouse TIEG can be found in Genbank accession Nos. AF0501010 and AF049879, respectively. The resulting clone was digested with EcoRI to yield a 14 kB fragment containing the full-length coding region. The entire fragment was mapped and sequences and found to contain 4 exons and 3 introns covering 7.1 kB, bounded by 6.6 kB of 5' flanking and 0.9 kB of 3' flanking sequence (see FIG. 1). The targeting vector was constructed by ligating a 3.5 kB XbaI fragment of the 5' flanking region (the 5' arm) upstream of the neomycin resistance cassette in vector 38locPNeo, and a 3.3 kB MscI-XbaI region containing exons 3 and 4 (the 3' arm) downstream from Neo (see FIG. 1). The complete targeting construct of 10.3 kB was excised from the resulting vector, 38loxPNeo/TIEG Example 2

Generating TIEG Mutant ES Cells and Null Mice

The 38loxPNeo/TIEG construct was transfected into murine ES cells isolated from the inner cell mass of a 3.5 day 129/SvJ mouse embryo by electroporation. Following expansion in selective growth medium, individual clones were screened by Southern blotting of EcoRI-digested genomic DNA using a probe to a region outside of the targeted locus (5' probe, see FIG. 1) to identify clones that contain the correctly targeted TIEG allele. In addition, a probe to the neomycin resistance gene (Neo$^r$) also was used.

One positive clone was identified, expanded, and confirmed by additional Southern analysis with the 3' probe. As shown in FIG. 1, correct homologous recombination results in a null mutation in which exons 1 and 2, as well as 2.3 kB of 5' flanking region of mTIEG (including transcription and translational start sites and the first 114 amino acids of the encoded TIEG protein) are replaced with the Neo$^r$ cassette. In addition, the Neo$^r$ cassette contains a poly A termination signal that terminates transcription of any aberrant mRNA transcript that might be synthesized from the mutant TIEG allele.

TIEG mutant ES cells were used to generate chimeric animals by injection into C57BL/6 (B6) blastocysts using established protocols. One male chimera was generated and subsequently bred to B6 females. DNA was isolated from tail biopsies of agouti-colored offspring and screened for germline transmission of the null allele by PCR and Southern blotting. Heterozygous male TIEG mutant mice were bred to B6 females to increase the colony size and subsequent heterozygous male and female mice were interbred to generate mouse embryo fibroblasts. Under gross examination, null animals were phenotypically normal. TIEG null mice are fertile and exhibit normal breeding. Fibroblasts from TIEG null mice readily immortalize in culture.

TIEG null mice develop overall cardiac hypertrophy and in particular, concentric left ventricular hypertrophy, as they age with an increase in purple collagen stain in the cardiac myocytes. Upon histological examination of heart tissue, there appears to be an increase in cell size and cell number in addition to the left ventricle hypertrophy. These changes were only seen in one-year old mice (n=3) and not the newborns.

Calvarial osteoblasts (OB) were isolated from 3 day old −/− and +/+ pups. These cells were cultured in vitro and assayed via RT-PCR for alkaline phosphatase, Cbfa-1, osteocalcin, and osterix gene expression. The −/− OB cells displayed a reduced expression of OB differentiation markers. The OB cells were differentiated in vitro with BMP-2 for 18 days. The OB from +/+ calvaria displayed several nodules in culture when stained with Alizarin red, whereas the OB from −/− calvaria showed no nodule formation. The −/− calvaria OB appear to have a defect in mediating the signals to differentiate in culture.

Figure 2:
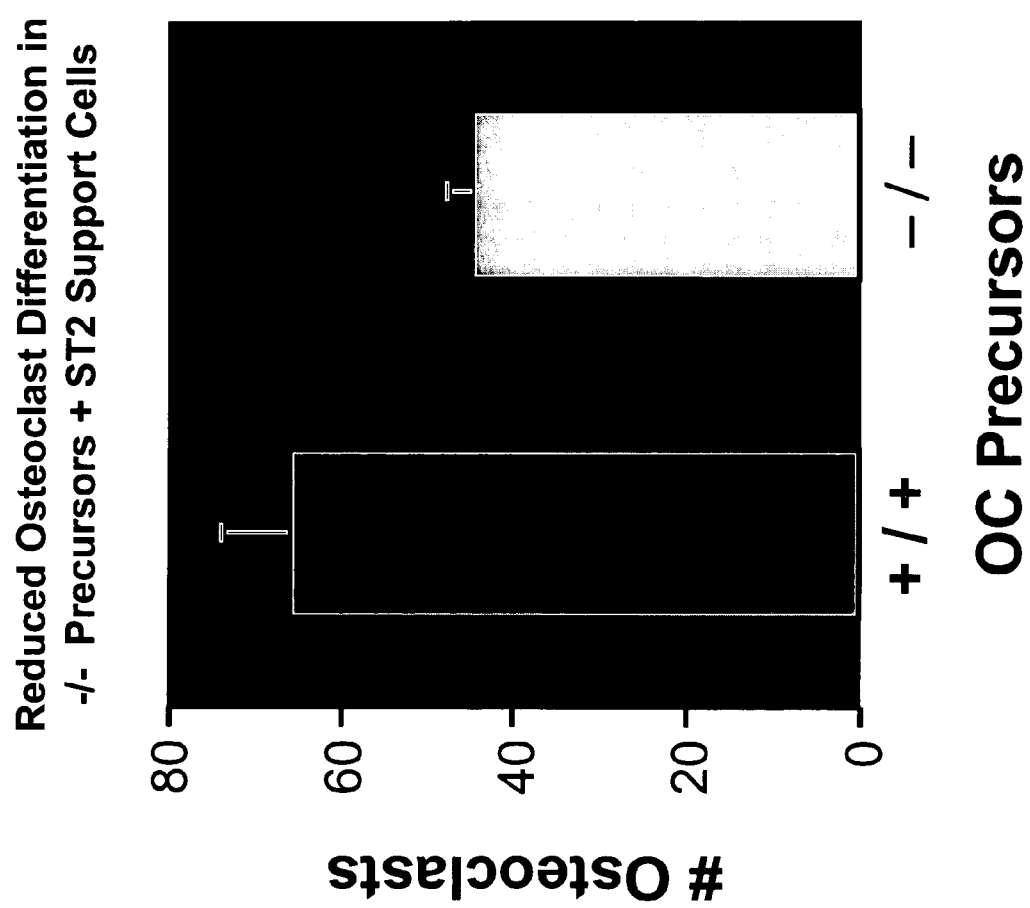
FIG. 2 is a graph depicting reduced osteoclast differentiation in −/− precursors and ST2 support cells.
Figure 3:
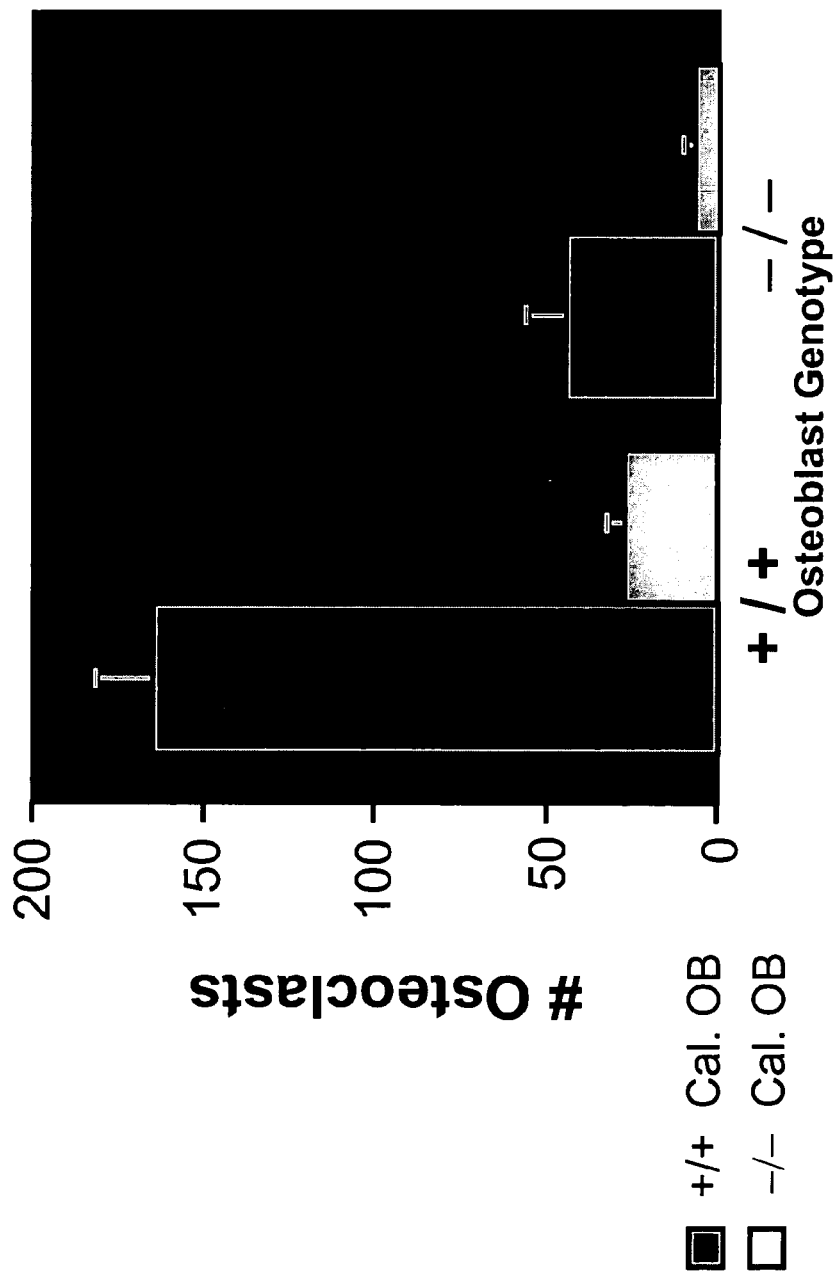
FIG. 3 is a graph depicting that loss of TIEG causes differentiation defects in both precursors and support cells.

To characterize the osteoclasts (OC) from +/+ and −/− mice, OC precursor cells were isolated from bone marrow. The interactions between OC precursors and calvarial OB from both −/− and +/+ mice were characterized. Bone marrow containing OC precursors were cultured with calvarial OB or ST2 stromal support cells in the presence of vitamin D ($10^{-8}$ M) and dexamethazone ($10^{-7}$ M) to generate OC-like cells. Cultures of −/− OC precursors with either ST2 or +/+ OB cells significantly decreased OC differentiation compared with +/+ marrow cells cultured with either support cell type (FIG. 2). These data support that there is a defect in OC precursors in −/− mice. Cultures of +/+ OC precursors cultured with −/− OB resulted in significantly lower differentiation (FIG. 3).

Figure 4:
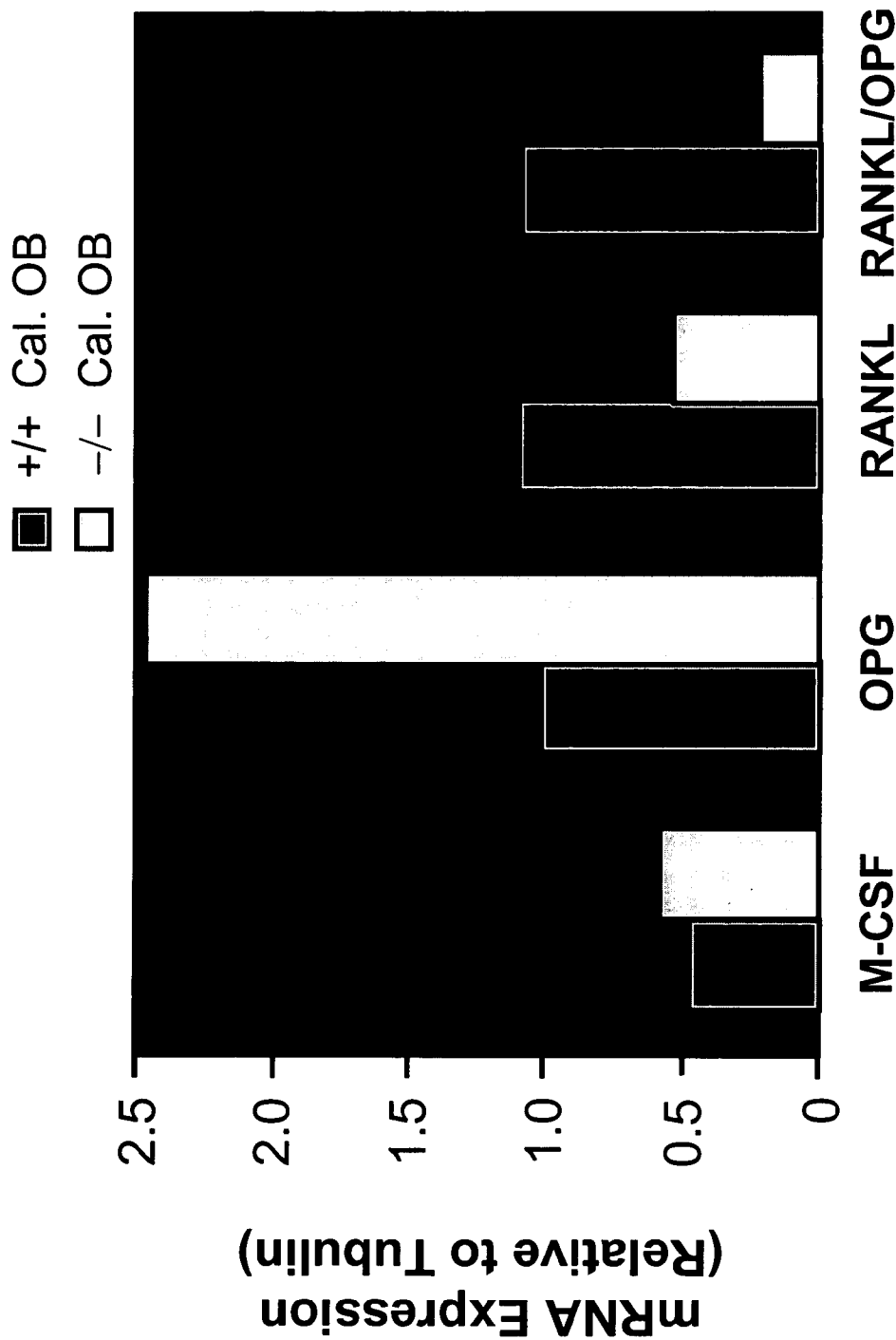
FIG. 4 is a graph depicting that the TIEG knockout reduces the RANKL/OPG ratio.

Examination of gene expression by real time PCR of the calvarial OB revealed decreased RANKL (receptor activator of NF-kappaB ligand) and increased OPG (osteoprotegerin) expression in the −/− calvarial OB compared with +/+ calvarial OB cells (FIG. 4). These data suggest that the decreased ability of −/− calvarial cells to support OC differentiation is due to a decrease in the ratio of RANKL to OPG in these cells.

To examine TGFβ responses in OC precursors during differentiation, spleen cell were cultured with RANKL and M-CSF during differentiation, with and without TGFβ. In +/+ cultures, there was a TGFβ dose-dependent increase in the number of OC. Interestingly, the −/− OC cells showed no impact of TGFβ on OC differentiation. These data support that TGFβ stimulation of OC differentiation is mediated by TIEG gene expression.

Example 3

TIEG Plays a Central Role in the Anti-Proliferative Response to TGFβ

The following experiments provide evidence that expression of TIEG is critical for the growth inhibitory effect of TGFβ. These results place TIEG as an important regulator of the physiological response to TGFβ and may provide the first insights into the mechanism by which cancer cells shift from a growth inhibitory to pro-metastatic response to TGFβ during the progression of cancer.

Methods and Materials

The tetracycline inducible TIEG overexpressing Hs578T cells were described previously and were cultured in DMEM/F12 (1:1) medium (Sigma, St. Louis, Mo., USA) containing 10% (v/v) FBS (Bio Whittaker, Walkersville, Md., USA) and 1× antibiotic-antimycotic solution (Invitrogen, Carlsbad, Calif., USA), 5 mg/L blasticidin S (Invitrogen) and 500 mg/L Zeocin(Invitrogen; Johnsen et al., *Oncogene* (2002) 21:5783-5790 and Johnsen et al., *J. Cell Biochem.* (2002) 87:233-241). Briefly, the Hs578T-Tet-TIEG cells were generated though the stable transfection with the tetracycline repressor plasmid pcDNA6/TR (Invitrogen) and a plasmid containing an amino-terminally Flag epitope tagged TIEG under the control of a modified Cytomegalovirus promoter containing three tetracycline operator sites (pcDNA4/TO, Invitrogen). Mouse embryo fibroblast cells were cultured in DMEM medium (Sigma) containing 10% FBS (v/v) and 1× antibiotic-antimycotic solution (Invitrogen). For transfections, cells were seeded in 12-well plates and transfected at 50% confluence with plasmid DNA using Lipofectamine Plus (Invitrogen) according to the manufacturer's directions. The CAGA12-MLP-Luc reporter construct has been described elsewhere (Dennler et al., *EMBO J.* (1998) 17:3091-3100).

Mouse embryo fibroblast (MEF) isolation: The development and description of TIEG null mice is provided herein. MEF cells were prepared from heterozygous TIEG null C57BL6×129/SvJ cross-bred female mice at 15 dpc using standard procedures and were maintained in DMEM medium as described above. MEF cells from wild-type and TIEG null embryos were identified by PCR genotyping and utilized for further studies.

Cell proliferation assays: Hs578T Tet-TIEG cells were seeded at 2,500 cells per well, and MEF cells were seeded at 1,600 cells/well in 96-well plates and incubated at 37° C. for 24 hours in normal culture medium. The medium was then replaced with 100 µL fresh medium or medium containing 1 µg/mL tetracycline (for Hs578TTet-TIEG cells) or 2 ng/mL TGFβ (for MEF cells). Cells were grown for an additional 48 hours, and the relative number of viable cells in each well was then determined using the CellTiter 96 AQueous One Solution Cell Proliferation Assay (Promega, Madison, Wis., USA). Briefly, 20 µL of Cell Titer 96 AQueous One Solution were added to each well, including three wells containing only medium for background substraction. The cells were then incubated at 37° C. for 30 minutes. The absorbance at 490 nm in each well was then determined using a SpectraMax 340 plate reader/spectrophotometer (Molecular Devices Corp., Sunnyvale, Calif.). This technique was determined to produce a linear relationship between the number of viable cells and the absorbance at 490 nm. Average data and standard deviation from twelve samples were compared to control treated cells and expressed as relative proliferation. Statistical analysis was performed using the student's t test.

Isolation of genomic DNA and genotyping: Genomic DNA was isolated using the DNeasy Tissue Kit (Qiagen, Valencia, Calif., USA) according to the manufacturer's instructions. DNA was eluted with 100 µL water, and 2 µL was used for genotyping by PCR. Genotyping by PCR was performed using the following primers: Neo-F, 5'-GAAT-AGCCTCTCCACCCAAGCGG-3' (SEQ ID NO:8); TIEG-Int2F, 5'-CCTCTAATTCCTCTCCTTGC-3' (SEQ ID NO:9); and TIEG-Ex3R, 5'-TGGTGGTTGCACAGT-TGGGGCATCAGCTG-3' (SEQ ID NO:10); where the wild-type allele produces a 270-bp band from primers TIEG-Int2F and TIEG-Ex3R, and the mutant allele produces a 350-bp band from primers Neo-F and TIEG-Ex3R. PCR reactions were performed using 40 cycles of 1 minute at 94° C., 2 minutes at 55° C. and 3 minutes at 72° C. Products were separated on 1.5% (w/v) agarose gels, and bands were visualized under ultraviolet light following staining with ethidium bromide.

Luciferase promoter reporter assays: Cell extracts were harvested using 300 µL of Passive Lysis Buffer (Promega). Luciferase assays were performed using the Dual-Luciferase Reporter Assay System (Promega), and samples were read on a Turner TD-20/20 luminometer. To correct for differences in transfection efficiency, firefly luciferase units were normalized relative to renilla luciferase units of the same sample. Corrected luciferase values were then expressed as a ratio (fold induction) relative to the vector control transfected cells.

Northern blot analysis and semi-quantitative RT-PCR: Northern blot analysis for TEG mRNA was performed as described elsewhere (Johnsen et al., *J. Cell Biochem.* (2002) 87:233-241). Semi-quantitative RT-PCR was performed as described elsewhere (Johnsen et al., *J. Cell Biochem.* (2002) 87:233-241) using the following primers and cycle numbers. Primers used were Smad7-Forward 5'-ACGCGCAC-CGCGTGC-CTCCTGCT-3' (SEQ ID NO:11), Smad7-Reverse 5'-CTAAGGTGATGGGGGTTG-CAGCACAC-CAGCTC-3' (SEQ ID NO:12), mGAPDH-Forward 5'-CACCATGGAG-AAGGCCGGGG-3' (SEQ ID NO:13), and mGAPDH-Reverse 5'-GACGGACACATTG-GGGG-TAG-3' (SEQ ID NO:14), and yield products of 201 bp (mTIEG), 236 bp (Smad7), and 418 bp (mGAPDH).

Western blot analysis: Cell extracts were harvested in RIPA buffer (phosphate buffered saline, 1% (w/v) Nonidet P-40, 0.5% (w/v) sodium deoxycholate, 0.1% (w/v) SDS) containing 100 µg/mL PMSF, 2 µg/mL aprotinin, 10 µg/mL leupeptin, and 500 µM sodium orthovanadate. Polypeptides were separated on a SDS 10% (w/v) polyacrylamide gel and blotted onto Protran nitrocellulose membranes (Schleicher and Schuell, Keene, N.H., USA). Actin, p21, and Flag epitope tagged polypeptides were detected with anti-Actin AC-40 (Sigma), anti-p21/Cip1 Ab-1 (Calbiochem, San Diego, Calif., USA), and anti-Flag M2 (Sigma) antibodies, respectively. Primary antibodies were detected by enhanced chemiluminescence (Amersham Pharmacia, Piscataway, N.J., USA) using horseradish peroxidase conjugated anti-mouse secondary antibodies (Sigma).

Results

The Hs578T breast cancer cell line has previously been shown to be growth inhibited by TGFβ (Arteaga et al., *Cancer Res.* (1988) 48:3898-3904) and was used herein as a model for TGFβ responsive breast cancer. A tetracycline inducible Hs578T TIEG over-expressing cell line was used to test the effects of TIEG on cellular proliferation (Johnsen et al., *Oncogene* (2002) 21:5783-5790). This system allows for the comparison of the same clonal cell line in the absence or presence of TIEG over-expression without the potential for artifacts due to clonal variation as is possible with constitutive over-expressing cell lines. In addition, numerous groups have demonstrated that doxycycline treatment alone does not significantly alter cellular proliferation (Burel et al., *Mol. Cell Biol.* (2001) 21:5577-5590 and Miyamoto et al., *J. Biol. Chem.* (2002) 277:4609-4617).

Figure 5A:
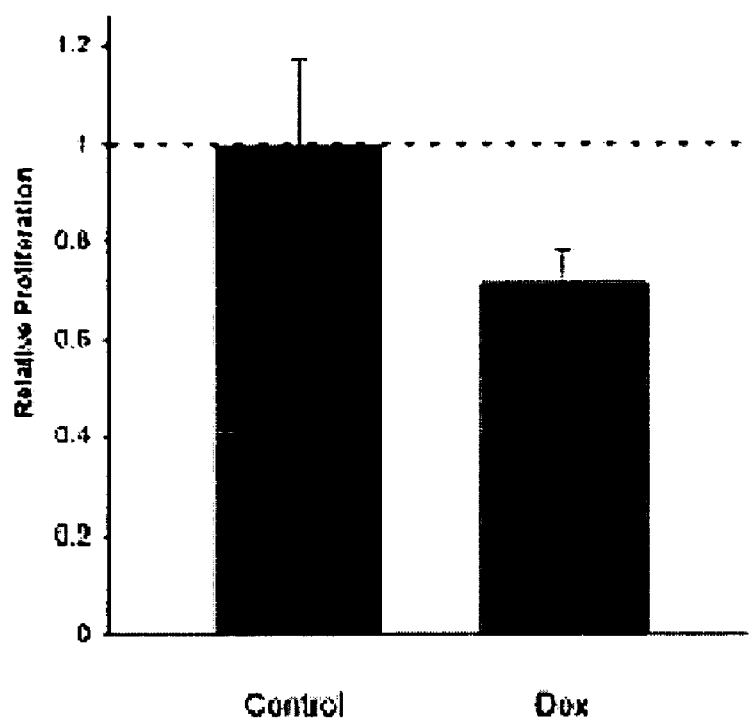
FIG. 5A is a bar graph plotting the relative number of viable Hs578T-Tet-TIEG cells grown in 96 well plates and measured after 48 hours of tetracycline treatment. Normalized values were graphed in relation to control treated cells (n=12). Error bars indicate S.D.P <0.005.

TEG over-expression decreases cellular proliferation by approximately 30 percent (FIG. 5A). In contrast to other cell types, in which TIEG overexpression induces apoptosis (Bender et al., *J. Neurosci. Res.* (2004) 75:344-352 and Chalaux et al., *FEBS Lett.* (1999) 457:478-82), no increase in apoptosis was observed in either cellular morphology studies or in DNA laddering experiments. TGFβ regulates cellular proliferation in numerous cell types by inducing cell cycle arrest, at least in part, through the upregulation of the cyclin dependent kinase inhibitor p21 (Moustakas et al., *Immunol. Lett.* (2002) 82:85-91). TIEG over-expression in Hs578T-Tet-TIEG cells was previously shown to increase moderately the basal expression of p21 and to increase dramatically the TGFβ induction of p21. The timecourse of p21 induction by TIEG, however, remains unclear.

Figure 5B:
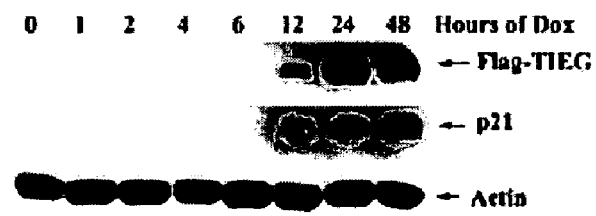
FIG. 5B is a photograph of a Western blot analysis using anti-FLAG M2, anti-p21, and anti-actin antibodies. Hs578T-Tet-TIEG cells were grown in 10-cm plates and treated with 1 µg/µL doxycycline for the indicated times.

The induction time course of p21 expression in relation to TIEG was compared by inducing the Hs578T-Tet-TIEG cells with tetracycline for various times. TIEG polypeptide levels begin to rise as early as 12 hours following addition of tetracycline to the growth medium and peaking at 24 hours (FIG. 5B). Interestingly, p21 polypeptide levels exhibited an identical induction pattern of induction, suggesting that TIEG increases p21 polypeptide levels very rapidly, perhaps suggesting that TIEG is directly involved in the regulation of p21 expression. Induction of p21 following TGFβ treatment is a complex process involving several individual response elements including Sp1 sequences and Smad polypeptides (Moustakas and Kardassis, *Proc. Natl. Acad. Sci. USA* (1998) 95:6733-8). It is conceivable that TIEG regulates p21 expression in multiple ways by not only increasing the activity of the Smad pathway (Johnsen et al., *Oncogene* (2002) 21:5783-5790; Johnsen et al., *J. Cell Biochem.* (2002) 87:233-241; and Johnsen et al., *J. Biol. Chem.* (2002) 277:30754-30759), but also through the up-regulation of promoter activity at Sp1 sequences (Blok et al., *Mol. Endocrinol.* (1995) 9:1610-20 and Noti et al., *J. Biol. Chem.* (2004) 279:26948-58).

Figure 6A:
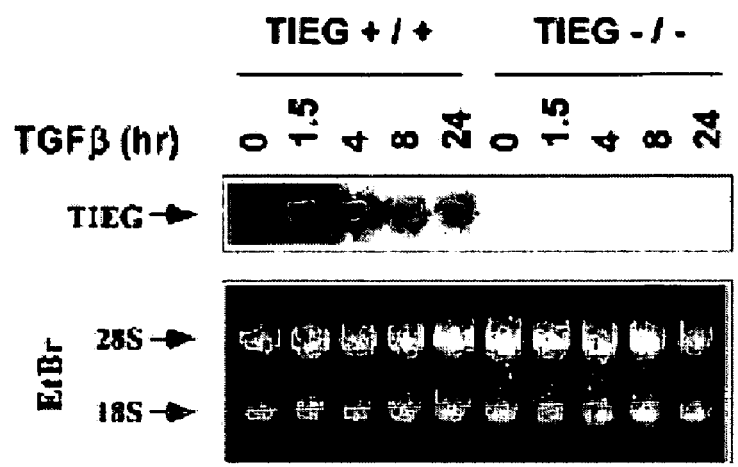
FIG. 6A is a photograph of a Northern blot analysis of mouse embryo fibroblast (MEF) cells treated with TGFβ1 (2 ng/mL) for the indicated times. Total RNA was extracted and analyzed by Northern blotting using a TIEG mRNA specific probe. Prior to Northern blotting, the gel was stained with ethidium bromide to verify equal loading.
Figure 6B:
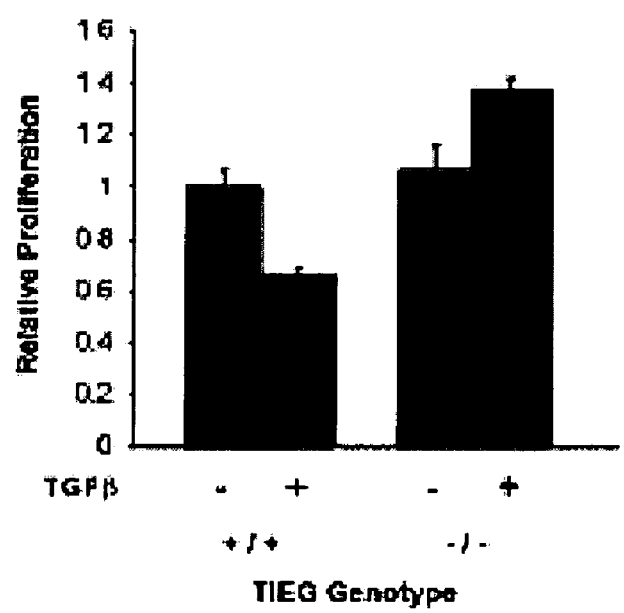
FIG. 6B is a bar graph plotting relative proliferation of Relative values for a representative experiment are shown (n=12). Error bars indicate S.D. P<0.005.

In order to definitively determine the role of TIEG in regulating TGFβ signaling and cellular proliferation, wild-type and TIEG null MEF cells were obtained from littermates from the crossing of two heterozygous (±) TIEG mutant mice. PCR and Southern blot analysis was used to genotype the MEF cells. TIEG is required for inhibition of proliferation by TGFβ. The TIEG null cells exhibited no detectable TIEG mRNA, while the wild-type cells exhibited both basal and TGFβ induced TIEG mRNA expression (FIG. 6A). Because TGFβ plays an important role in regulating cellular proliferation, and since over-expression of TIEG also decreases cellular proliferation (FIG. 5A), TIEG was tested to determine whether it is required for the inhibition of proliferation by TGFβ. Indeed, while TGFβ decreases proliferation in wild-type MEF cells by 34 percent, TGFβ increases cell proliferation by 31 percent in the TIEG null MEF cells (FIG. 6B). These results suggest that TIEG plays an integral role in the regulation of cell proliferation by TGFβ.

Figure 7A:
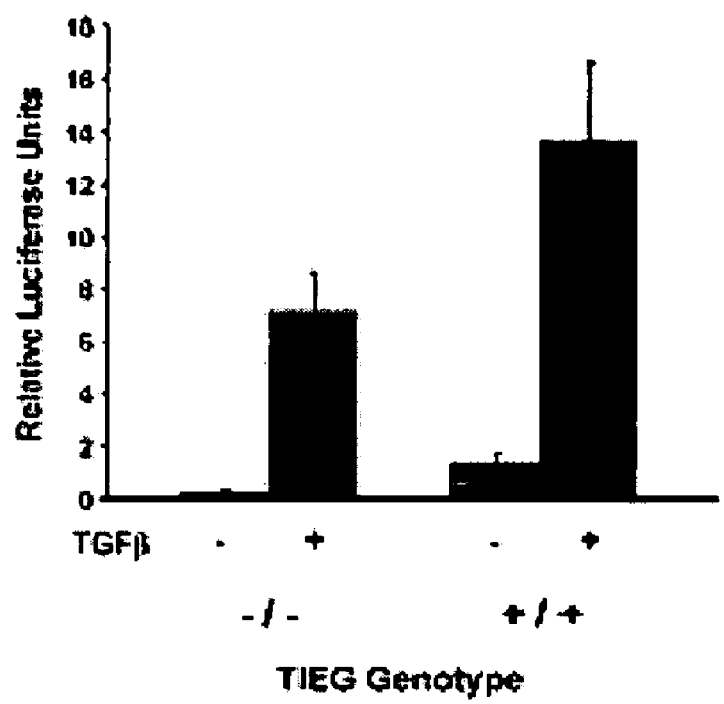
FIG. 7A is a bar graph plotting the relative luciferase units for wild-type (+/+) and TIEG null (−/−) MEF cells grown in the presence (+) or absence (−) of 2 ng/mL TGFβ1. The cells were grown in 12-well plates and transfected with the CACA12-MLP-Luc (0.5 µg) reporter construct and the internal control plasmid, phRGTK (50 ng). 24 hours after transfection cells were switched to serum-free medium containing 2 ng/mL TGFβ1. Normalized relative luciferase values are shown for a representative experiment (n=6). Error bars indicate S.D.
Figure 7B:
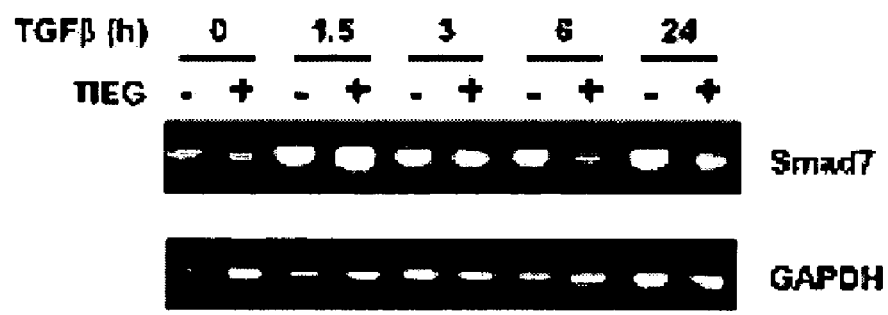
FIG. 7B is a photograph of an RT-PCR experiment. Total RNA isolated from wild-type (+) and TIEG null (−) MEF cells treated with TGFβ1 for the indicated times was reverse transcribed, and PCRs were performed in duplicate for Smad7 and GAPDH mRNA. The PCR products were separated on 1.5% (w/v) agarose gels and visualized with ethidium bromide.

Over-expression of TIEG enhances the induction of a synthetic Smad binding element reporter construct (CAGA12-MLP-Luc) as well as the induction of endogenous TGFβ regulated genes (Johnsen et al., *Oncogene* (2002) 21:5783-5790; Johnsen et al., *J. Cell Biochem.* (2002) 87:233-241; and Johnsen et al., *J. Biol. Chem.* (2002) 277:30754-30759). Experiments were performed to determine if TGFβ signaling is deregulated in TIEG null cells. The TIEG null MEF cells exhibited decreased basal and TGFβ-induced reporter gene activity compared to wild-type cells (FIG. 7A). These results suggest that loss of TIEG abrogates the activity of the Smad pathway in the presence of autocrine or exogenous TGFβ stimulation. Previous reports have indicated that TIEG enhances TGFβ/Smad signaling, at least in part, by transcriptionally repressing Smad7 gene expression (Johnsen et al., *Oncogene* (2002) 21:5783-5790 and Bender et al., *J. Neurosci. Res.* (2004) 75:344-352). The effects of loss of TIEG on Smad7 gene expression was tested. In the wild-type MEF cells, Smad7 mRNA levels rapidly increase following TGFβ treatment with levels decreasing by 3-6 hours. In contrast, Smad7 levels remain elevated at 12 and 24 hours in TIEG null cells (FIG. 7B). These results support a role for TIEG in the regulation of the TGFβ/Smad pathway through the repression of the inhibitory Smad7 gene.

In summary, these results demonstrate that TIEG plays an integral role in the regulation of cellular proliferation by TGFβ. Furthermore, loss of TIEG expression has dramatic effects on the induction of Smad dependent transcription. The results also suggest a mechanism by which the loss of TIEG may lead to, or enhance, the development of breast and other types of cancer. Previous data showed that TIEG polypeptide levels decrease throughout the progression of breast cancer where advanced stages of breast cancer exhibit no detectable TIEG polypeptide expression (Subramaniam et al., *J. Cell. Biochem.* (1998) 68:226-36). Interestingly, TGFβ has been observed to have dramatically different effects on breast cancer cells than normal mammary epithelial cells suggesting that there is an alteration in the responses elicited by TGFβ between normal and cancerous cells (Koli and Arteaga, *J. Mammary. Gland. Biol. Neoplasia.* (1996) 1:373-380). The results provided herein support a hypothesis that the loss of TIEG plays an important role in the loss of the growth inhibitory properties of TGFβ during the progression of cancer. Additional studies using the TIEG null mice can help establish the importance for TIEG in vivo.

Example 4

TIEG Null Mouse-Derived Osteoblasts are Defective in Mineralization and in Support of Osteoclast Differentiation In Vitro This example expands on the information provided in Example 2.

Methods and Materials

Calvarial Osteoblast isolation: Calvarial osteoblasts were isolated from 1-3 day old neonatal mouse pups. In brief, 1-3 day old mouse pups that were born to heterozygous TIEG null C57BL6/129 parents were euthanized using $CO_2$. The calvaria was dissected out and washed several times with phosphate buffered saline (PBS) to remove the blood cells. The calvaria were minced and digested in Hank's balanced saline (HBS) containing bovine serum albumin (4 mg/mL) and collagenase type-2 (4 mg/mL) for 10 minutes at 37° C. The cells obtained from the third digest was centrifuged at 221×g for 5 minutes, and the cells were resuspended in αMEM containing 10% (v/v) fetal bovine serum and grown in culture dishes. The calvarial osteoblasts obtained were used as support cells for osteoclast precursors and for osteoblast differentiation studies.

Osteoblast mineralization studies: Primary calvarial osteoblasts obtained from TIEG +/+ and TIEG −/− null mice were plated onto 12 well plates at a low density and grown until confluency. The cells were then shifted to differentiation media containing ascorbic acid (50 μg/mL) and β-glycerol phosphate (4 mM). The cells were treated with vehicle or bone morphogenic protein-2 (BMP2) (100 ng/mL) every third day and allowed to mineralize for 18 days. Once the bone nodules were visible, the cells were washed twice with PBS and fixed in 10% (v/v) neutral buffered formalin overnight. The fixed cells were stained with 2% (w/v) alizarin red for 10 minutes. Finally, the cells were washed with distilled water to remove excess stain and visualized for bone nodules.

Northern blot analysis and semi-quantitative RT-PCR: Northern blot analysis to measure the TIEG mRNA levels in TIEG +/+ and TIEG −/− osteoblasts were performed as described elsewhere (Subramaniam et al., *Nucleic Acids Res.* (1995) 23:4907-4912). Semi-quantitative RT-PCR was performed to measure the osteoblast specific marker genes in cultured calvarial osteoblasts as described elsewhere (Rickard et al., *J. Cell. Biochem.* (2003) 89:633-646). The primers used were: mTIEG-F 5'-GTCTCAGT-GCTC-CCGTCTGT-3' (SEQ ID NO:15); mTIEG-R 5'-CCAC-CGCTTCAAAGTCACTC-3' (SEQ ID NO:16); alkaline phosphatase-F 5'-TCTCAACTGTTCTAGTTCCT-3' (SEQ ID NO:17); alkaline phosphatase-R 5'-TTGGGTCATTTC-CACATGC-3' (SEQ ID NO:18); Type 1A Col.-F 5'-TCTC-CACTCTTCTAGTTCCT-3' (SEQ ID NO:19); Type 1A Col.-R 5'-TTGGGTCATTTCCACATGC-3' (SEQ ID NO:20); ostrix F 5'-TGAGGAAGAAGCCCATTCAC-3' (SEQ ID NO:21); ostrix R 5'-ACTTCTTCTCC-CGGGT-GTG-3' (SEQ ID NO:22); osteocalcin F 5'-TCTGA-CAAACCTTCATGTCC-3' (SEQ ID NO:23); osteocalcin R 5'-AAATAGTGATACCGTAGATGCG-3' (SEQ ID NO:24); GAPDH F 5'-CACCATGGAGAAGGCCGGGG-3' (SEQ ID NO:25); GAPDH R 5'-GACGGACACATTGGGGG-TAG-3' (SEQ ID NO:26).

Western blot analysis: To determine the levels of TIEG polypeptide in TIEG −/− mice, liver tissue was collected from TIEG +/+ and TIEG −/− mice. Equal amounts of the tissue were homogenized in ice cold buffer containing 1% (v/v) NP40, 10% (v/v) gycerol, 137 mM NaCl, 20 mM Tris pH 7.4, 20 mM NaF, 1 mM sodium pyrophosphate, 1 mM orthovanadate, and protease inhibitor cocktail mix (Roche Diagnostics, Mannheim, Germany). The homogenate was centrifuged at 13,200×g for 20 minutes. The polypeptide quantitation was performed on the supernatant. One mg of the tissue lysate was immunoprecipitated with 8 µg of TIEG specific polyclonal antibody. The immunoprecipitates were separated on 5-15% (w/v) SDS-PAGE, and western blot was performed with a TIEG-specific polyclonal antibody.

Cell proliferation assay: TIEG +/+ and TIEG −/− calvarial osteoblasts were seeded at 6400 cells/well on 96 well plates and grown for 24, 48, and 72 hours at 37° C. The proliferation of these cells was measured using the Cell Titer 96 Aqueous One Solution Cell Proliferation Assay (Promega, Madison, Wis.). Average results from six replicates were compared between TIEG +/+ and TIEG −/− calvarial osteoblasts.

Southern blot analysis and genotyping: Genomic DNA was isolated from mouse tail using the DNeasy tissue kit (Qiagen, Valencia, Calif.). Twenty micrograms of the genomic DNA was digested with EcoRI and separated on a 0.8% (w/v) Agarose gel. Southern blot analysis was performed from digested DNA as described elsewhere (Sambrook et al., (1982) *Molecular cloning: a laboratory manual*, p. 382-389. In: Cold Spring Harbor Laboratory Press). The blot was probed with [$^{32}$P]-labeled 5'-probe: 0.8 kb EcoRI/XbaI fragment from subclone Eco TIEG. Genotyping by PCR was performed using the following primers: KONEOF1, 5'-CTAAAGCGCATGCTCCAGACTGCC-3' (SEQ ID NO:27); Intron 2F, 5'-CCTCTAATTCCTCTCCT-TGC-3' (SEQ ID NO:28); Exon 3R1, 5'-TGGTGGTTGCA-CAGTTGGGCATCAGCTG-3' (SEQ ID NO:29). PCR was performed at 1 minute at 94° C., 2 minutes at 55° C., and 3 minutes at 72° C. for a total of 40 cycles. The PCR products were separated on a 1.5% (w/v) agarose gel, and the gels were stained with ethidium bromide and photographed.

In vitro Osteoclast Differentiation with Calvarial Support Cells: Calvarial cells were plated at $4\times10^4$ cells/well on a 48 well plate (Fisher, Pittsburgh, Pa.) 24 hours prior (Day 1) to the addition of osteoclast precursors ($1.5\times10^6$ marrow mononuclear cells or $4.8\times10^7$ spleen cells per plate) and harvested as described elsewhere (Gingery et al., *J. Cell. Biochem.* (2003) 89:165-179). Precursors were added to the stromal cells (Day O) using α-modified Minimal Essential Medium (Gibco BRL, Grand Island, N.Y.) supplemented with 10% FBS, 1% antibiotic/antimycotic, $1\times10^{-7}$ M dexamethazone (Sigma Chemical Co., St Louis, Mo.), and $1\times10^{-5}$ M vitamin D3 (BioMol, Plymouth Meeting, Pa.) with or without the addition of 30 ng/mL of RANKL and/or 25 ng/mL M-CSF as indicated in the figure legends. The media was changed every three days. On day 9, the co-cultures were washed three times with 1× phosphate buffered saline (1× PBS −1.7 mM $KH_2PO_4$, 5 mM $Na_2HPO_4$, 150 mM NaCl, pH to 7.4) and fixed with 1% paraformaldehyde in 1× PBS. After incubating for 30 minutes at room temperature in fixative, the cells were rinsed with water three times and stored in water at 4° C. until they were evaluated for differentiation as follows.

Tartrate resistant acid phosphatase (TRAP) staining was used to visualize differentiated cells according to manufacturer's directions (Sigma Chemical Co., St. Louis, Mo.). The number of mononuclear and multinucleated TRAP positive cells were counted using an Olympus inverted microscope at 200× magnification.

Real Time Polymerase Chain Reaction Analyses: Calvarial cells were plated into 6 well plates at a density of $6.4\times10^5$ cells/well and treated with $10^{-7}$ M 1, 25-dihydroxyvitamin D3 and $10^{-7}$ M dexamethazone for 3 days. RNA was isolated using Trizol reagent according to manufacturer's protocol (Invitrogen, Carlesbad, Calif.). Following LiCl precipitation to remove DNA, cDNA was synthesized by standard protocol: One µg total RNA was heat denatured at 68° C. for 15 minutes in reverse transcription reaction buffer (50 mM Tris-HCl, 75 mM KCl, 3 mM $MgCl_2$, 50 mM DTT, 1 µM dNTPs, 500 ng oligo- dT primer). Following heat denaturation, 1 unit of MMLV-RT (Invitrogen) was added, and the mixture incubated at 37° C. for 45 minutes followed by a 68° C. incubation for an additional 15 minutes. Two µL of the resultant cDNA was used for each reaction as follows: PCR buffer (20 mM Tris-HCl, 50 mM KCl, 3 mM $MgCl_2$), 300 nM of both the upstream and downstream primers, and 1 unit of Taq Polymerase (Promega, Madison, Wis.). As a control, tubulin was amplified simultaneously in separate reactions. Message levels were examined using the BioRad iCycler according to the manufacturer's specifications. The amount of target cDNA in the sample, relative to tubulin, was calculated using the formula $2^{\Delta\Delta Ct}$, where ΔΔCt is the fractional cycle number difference between the target and tubulin levels. The results were calculated as the relative quantification of the target gene compared to a control (vehicle without vitamin D or dexamethazone) treatment. The primers were as follows: M-CSF-F—5'-CTCTGGCTG-GCTTGGCTTGG-3' (SEQ ID NO:30); M-CSF-R—5'-GCAGAAGG-ATGAGGTTGTG-3' (SEQ ID NO:31); OPG-F—5'-ACGGACAGCTGGCACACCAG-3' (SEQ ID NO:32); OPG-R—5'-CTC ACACACTCGGTTGTGGG-3' (SEQ ID NO:33); RANKL-F—5'-GGAGGACCATGAAC-CCTTTCC-3' (SEQ ID NO:34); RANKL-R—5'-GCTG-GCTGCTGCTTCACTGG-3' (SEQ ID NO:35); Tubulin-F—5'-CTGCTC-ATCAGCAAGATCAGAG-3' (SEQ ID NO:36); and Tubulin-R—5'-GCATTATAGG-GXTCCAC-CACAG-3' (SEQ ID NO:37).

Microarray Analysis: Calvarial osteoblasts isolated from TIEG +/+ and TIEG −/− mice were allowed to grow to near confluency and then treated with either vehicle or 2 ng/mL TGFβ for 24 hours in duplicate. Total RNA was isolated using Trizol Reagent (Invitrogen), and 4 µg of RNA was used in microarray analysis on the mouse MOE430A microarray (Affymetrix, Santa Clara, Calif.) containing oligonucleotide probes for approximately 23,000 mouse sequences. Preparation of the labeled cDNA and microarray hybridization was performed by a microarray core facility. Analysis of the gene expression profiles was performed using the GeneSpring 6.1 software (Silicon Genetics, Redwood City, Calif.). Only those genes differentially expressed ≦or ≧2-fold were considered in the analysis.

Results

Phenotype of TIEG null mice: Under gross examination, the TIEG null mice were phenotypically normal, and the breeding characteristics appeared to be normal. Detailed examination of all major organs revealed that the TIEG null male mice exhibited hypertropic hearts, but only in the aged mice. Fibroblasts and calvarial osteoblasts generated from the TIEG −/− mice were readily immortalized in culture, reflecting the loss or reduction of the TGFβ signaling pathway due to the loss of TIEG. Histomorphometric analysis of bones, obtained from 6-week and 4-month animals, did not reveal a bone phenotype. To further characterize the role of TIEG in osteoblast gene expression and differentiation, calvarial osteoblasts were isolated from TIEG +/+ and TIEG −/− mice and cultured in vitro.

Figure 8:
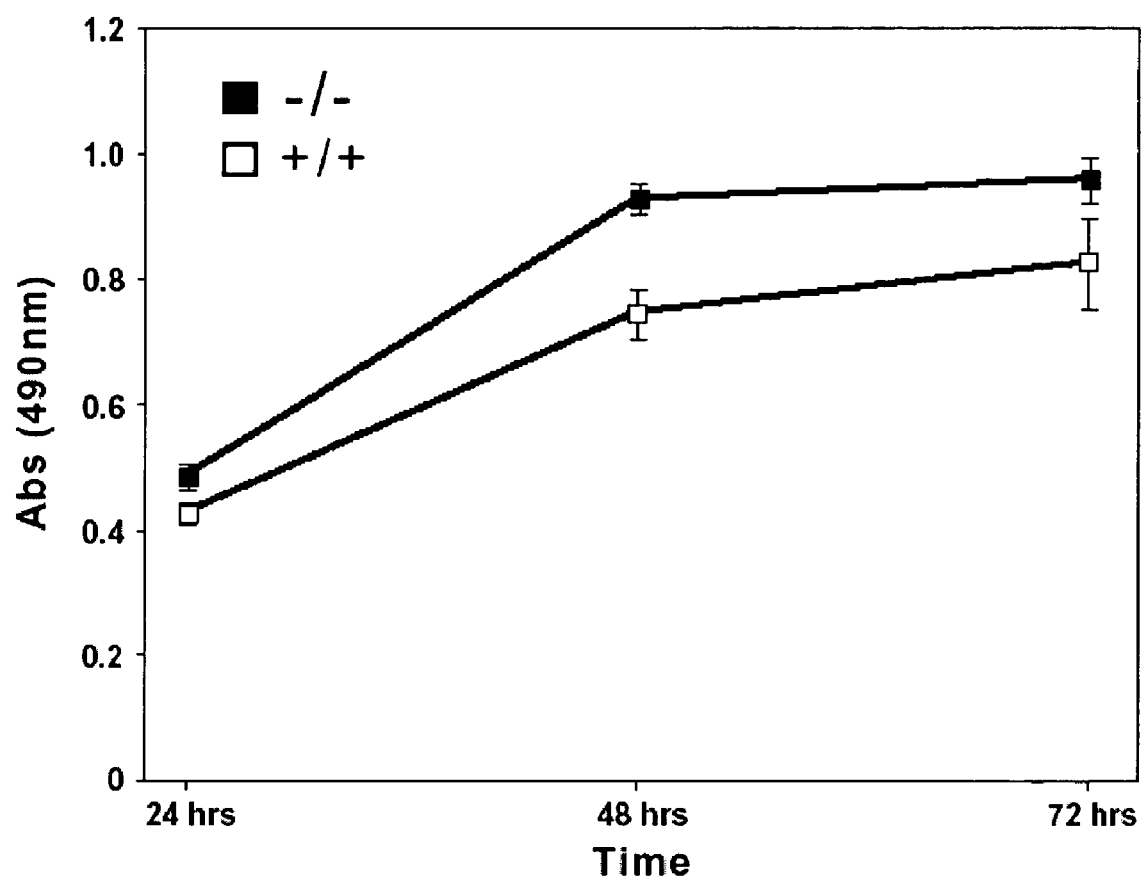
FIG. 8 is a line graph plotting cell proliferation (absorbance at 490 nm) of TIEG +/+ and TIEG −/− calvarial osteoblasts plated onto 96 well plates and grown for 24, 48, and 72 hours at 37° C. An average of six replicates of each were graphed.

Calvarial osteoblast cell proliferation: Calvarial osteoblasts from TIEG +/+ and TIEG −/− mice were plated onto a 96-well cell culture dish, and proliferation rates were measured at 24, 48, and 72 hours. The proliferation rate of TIEG −/− calvarial osteoblasts were slightly higher than that of TIEG +/+ osteoblasts (FIG. 8).

Mineralization of calvarial osteoblasts in culture: The treatment of osteoblasts in culture with bone morphogenic protein-2 (BMP2) induces mineralized bone nodule formation. To compare bone nodule formation from TIEG +/+ and TIEG −/− calvarial osteoblasts in culture, the cells were grown in differentiation media for 18 days with BMP2 treatment every third day. The TIEG +/+ osteoblasts generated distinctive nodule formation in culture, whereas the TIEG −/− osteoblasts lacked the capacity to form mineralized nodules.

Figure 9:
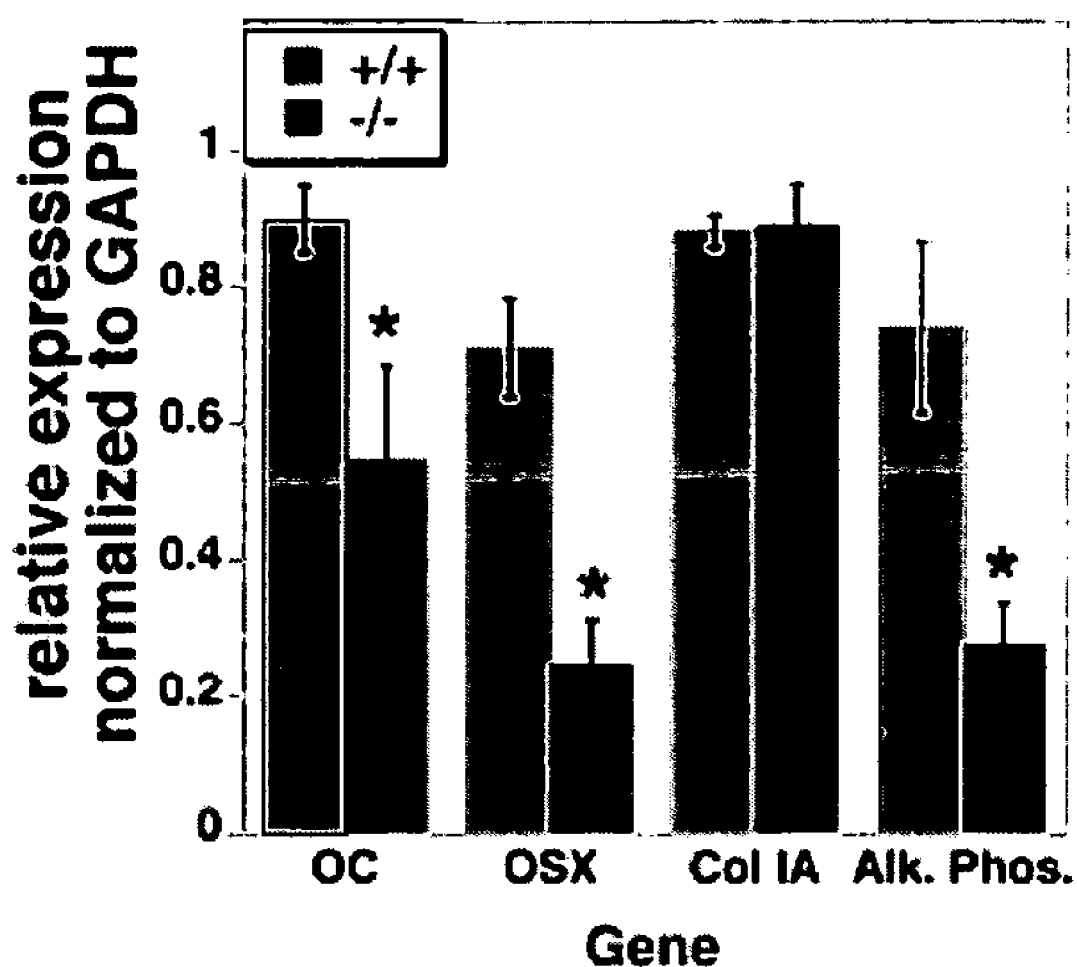
FIG. 9 is a bar graph plotting the relative mRNA expression levels for osteocalcin (OC), ostrix (OSX), type I collagen (Col IA), and alkaline phosphatase (Alk. Phos.) in TIEG +/+ and TIEG −/− calvarial osteoblasts grown in culture. RT-PCR was performed on five separate calvarial RNA isolates, and the results scanned and quantitated using NIH Image. The data are the mean ±SEM of these analyses normalized to GAPDH expression. * indicates p<0.05 comparing TIEG +/+ to TIEG −/− calvarial osteoblasts.

TIEG −/− Calvarial Cells Are Defective in Expression Of Osteoblastic Genes III Vitro: The osteoblastic gene expression patterns of the TIEG +/+ and TIEG −/− calvarial cells were examined. Total RNA was used to perform log phase RT-PCR using standard techniques. Analysis was performed on five separate calvarial isolates, and the results scanned and quantitated using NIH Image. The data were normalized to GAPDH expression. Osteocalcin, ostrix, and alkaline phosphatase were significantly lower in the TIEG −/− calvarial cells when compared to the TIEG +/+ cells (FIG. 9). A similar pattern was observed with Cbfa-1, but significant variations in expression between cultures decreased its significance. There was no significant difference in type I Collagen (Col IA) and GAPDH mRNA levels, demonstrating that TIEG regulates only selected genes. These results suggest that the lack of TIEG in the calvarial osteoblast cells reduces the ability of these cells to create bone matrix via a deficiency in the expression of select bone related (osteoblastic) gene expression.

Figure 10:
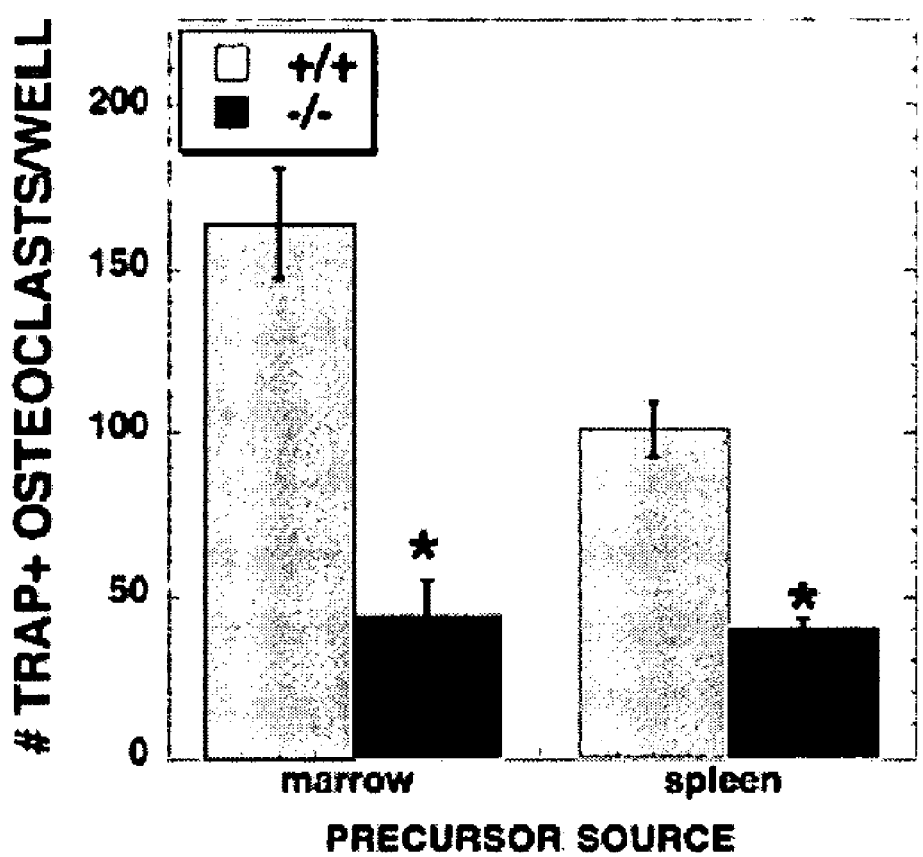
FIG. 10 is a bar graph plotting the number of TRAP+ osteoclasts per well for neonatal calvaria-derived osteoblasts from TIEG +/+ or TIEG −/− mice cultured with either marrow or spleen osteoclast precursors from TIEG +/+ mice in the presence of vitamin D and Dexamethazone for 9 days. The data are the mean ±SEM of three replicate wells from one experiment. The experiment was performed 4 times, and these data are representative of the results. * indicates p<0.05 comparing TIEG +/+ to TIEG −/− calvarial cells.

Osteoblastic cells from TIEG −/− mice are defective in supporting osteoclast differentiation: Osteoblastic cells from TIEG +/+ and TIEG −/− mice were plated. Marrow or spleen tissues from TIEG +/+ mice were used as a source of wild-type osteoclast precursors. Following co-culture in the presence of vitamin D3 and dexamethazone for 9 days, the number of osteoclasts were determined. Compared to TIEG +/+ osteoblastic cells, cells from TIEG −/− mice are significantly less able to support osteoclast differentiation from either marrow or spleen precursors (FIG. 10).

Figure 11:
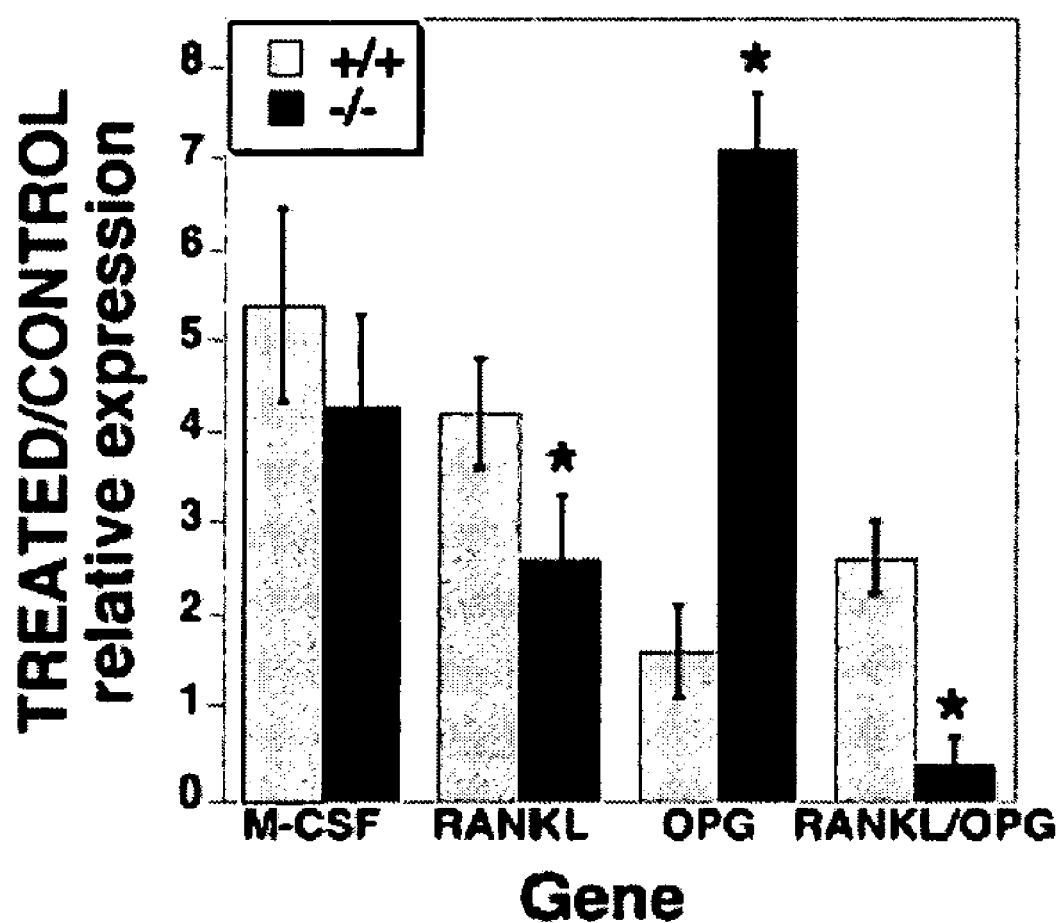
FIG. 11 is a bar graph plotting the relative expression levels of M-CSF, RANKL, and OPG in TIEG −/− cells or TIEG +/+ cells cultured with vitamin D and dexamethazone. Real Time PCR was performed to quantitate the M-CSF, RANKL, and OPG expression relative to tubulin, and the ratio of RANKL to OPG was determined. * indicates p<0.05 comparing TIEG +/+ to TIEG −/− calvarial cells.

The RANKL/OPG Ratio Is Lower In TIEG −/− Cells than in TIEG +/+ Cells: Osteoblastic cells support osteoclast differentiation by producing the enhancers of OC differentiation, M-CSF and RANKL, with a balanced production of the inhibitor of OC differentiation, osteoprotegerin (OPG), a RANKL decoy receptor (Khosla, *Endocrinology* 2001 142: 5050-5055). Since vitamin D and dexamethazone were used to stimulate RANKL and M-CSF expression while repressing OPG expression in support cells, the impact of these hormones on calvarial cell gene expression was examined using Real Time PCR. Reduced levels of RANKL mRNA and increased levels of OPG mRNA were detected in the TIEG −/− calvarial cells as compared to TIEG +/+ cells (FIG. 11). A significant reduction in the RANKL to OPG ratio was detected in the TIEG −/− cells as compared to TIEG +/+ cells. In contrast, there is no apparent impact of lack of TIEG on M-CSF gene expression. Examination of secreted polypeptide levels using a cytokine array (Ray Biotech, Calif.) revealed that there was 2-fold less OPG in TIEG +/+ cultures as compared to TIEG −/− cultures, whereas there was 3.9-fold more M-CSF in the TIEG +/+ cultures as compared to TIEG −/− cell cultures.

Figure 12:
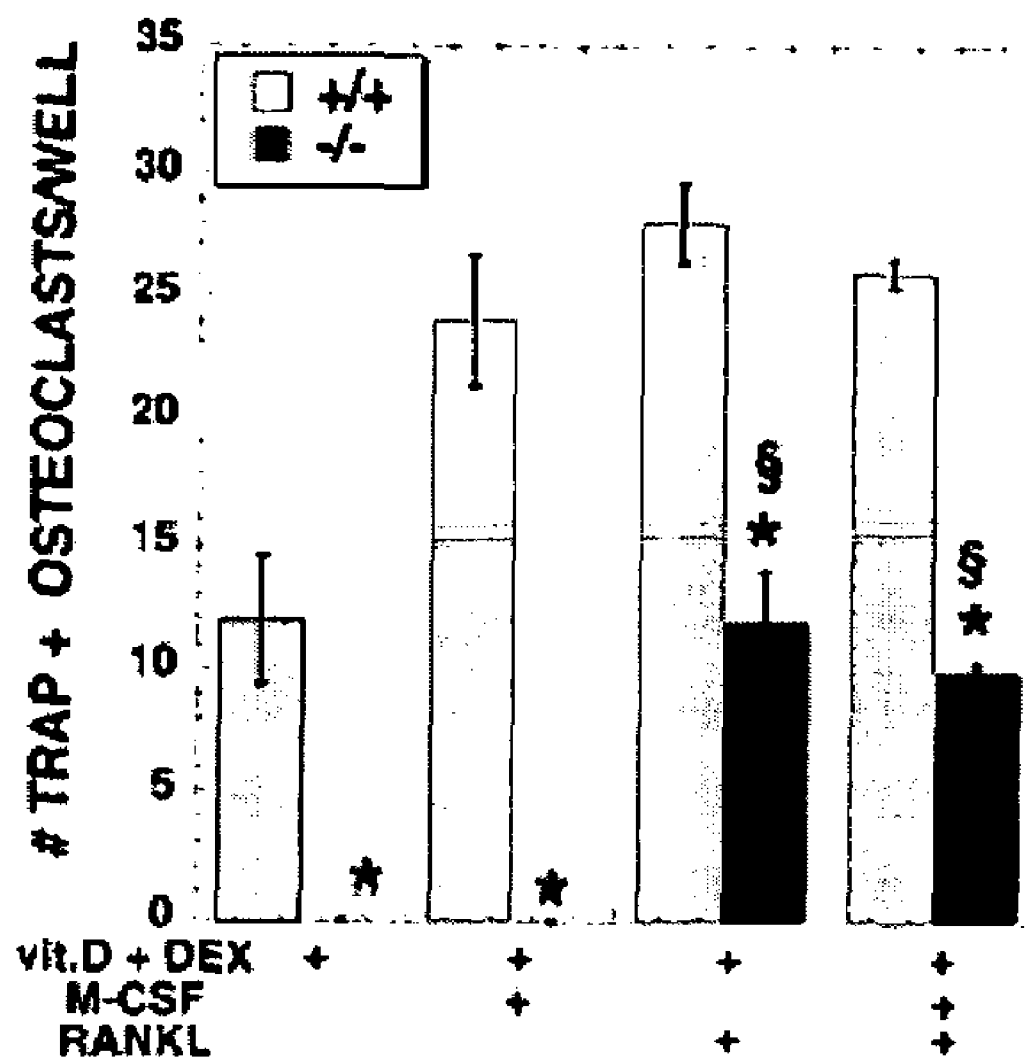
FIG. 12 is a bar graph plotting the number of TRAP + osteoclasts per well for TIEG +/+ and TIEG −/− calvarial cells cultured with TIEG +/+ marrow in the presence of the indicated hormones or growth factors. * indicates p<0.05 comparing TIEG +/+ to TIEG −/− calvarial OB cells, and § indicates p<0.05 comparing vitamin D and dexamethazone alone to addition of the indicated hormones or growth factors.

Replenishing the RANKL Partially Restores the TIEG −/− Calvarial Cell's Ability To Induce Osteoclast Differentiation. The above results suggest that either altering the M-CSF (due to polypeptide secretion differences) or the ratio of RANKL to OPG (due to gene and polypeptide differences) could reverse the reduced capacity of the TIEG −/− calvarial cells to support osteoclast differentiation. To examine these possibilities, TIEG +/+ and TIEG −/− calvarial osteoblast cells were cultured with TIEG +/+ marrow in the presence of various combinations of the growth factors. Addition of 30 ng/mL RANKL partially, but not completely, restored differentiation (FIG. 12). Ten ng/mL M-CSF alone or in conjunction with RANKL treatment had no additional impact on osteoclast differentiation over that of the addition of RANKL alone. Additional experiments with higher RANKL concentrations did not increase differentiation above that measured with 30 ng/mL.

Figure 13:
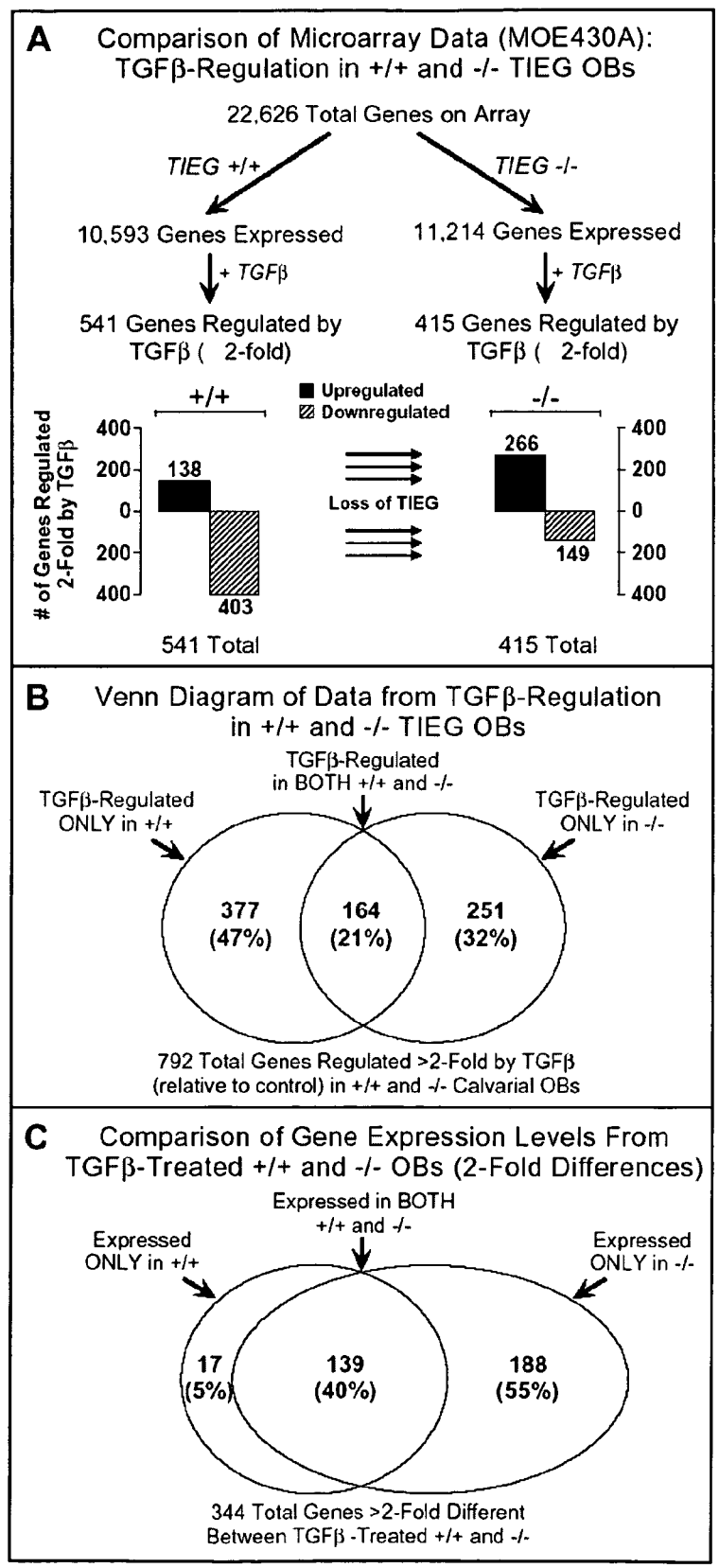
FIG. 13 is an outline of a gene microarray analysis. Panel A) Calvarial osteoblasts were isolated from TIEG +/+ and TIEG −/− mice and cultured in vitro. Some samples were treated with 2 ng/mL TGFβ for 24 hours in duplicate. RNA was then isolated from TGFβ and vehicle treated samples and subjected to microarray using the MOE430A microarray containing 22,626 total genes. The data was analyzed, and the number of genes expressed and regulated by TGFβ is indicated. Panel B is a comparison of the TGFβ-regulated genes between TIEG +/+ and TIEG −/− osteoblasts with the data presented as a Venn diagram as to those genes regulated by TGFβ in TIEG +/+ or TIEG −/− only, and those regulated in both genotypes. Panel C is a comparison of TGFβ regulated genes between osteoblast cells from TIEG +/+ mice and TIEG −/− mice with the data presented as a Venn diagram as to those genes expressed in TIEG +/+ or TIEG −/− cells.

Microarray analysis of TIEG +/+ and TIEG −/− osteoblasts: The transcription factor TIEG affects the expression of genes, such as Smad7 (Johnsen et al., *Oncogene* (2002) 21:5783-5790) and CD11d promoter (Noti et al., *J. Biol. Chem.* (2004) 279:26948-58) by binding a specific DNA-binding motif and regulating transcription. The loss of TIEG expression could elicit changes in gene transcription in those genes dependent on TIEG for regulation. The gene expression profiles of calvarial OB cells from TIEG +/+ and TIEG −/− mice treated with TGFβ were examined. Only 4-5% of the total genes expressed in OBs from either genotype were regulated at least 2-fold (up or down) by TGFβ treatment (FIG. 13A). As expected, 403 genes were repressed by TGFβ treatment in the TIEG +/+ OB cells, while only 149 genes were repressed by TGFβ treatment of the TIEG −/− OB cells. The reverse pattern occured with the genes that are induced by TGFβ with 138 in the TIEG +/+ OB cells and 260 in the TIEG −/− OB cells. This is expected, since TIEG is reported to be a general repressor of transcription with minor cases of gene induction. This suggests that the major role of TIEG is a repressor of transcription, since the loss of TIEG results in a decrease in gene repression. Twenty-one percent of the TGFβ-regulated genes were commonly regulated by the OB cells of both genotypes, whereas 47% and 32% are regulated exclusively in the TIEG +/+ and TIEG −/− OBs, respectively (FIG. 13B). Thus, the loss of TIEG causes the loss of regulation of 126 genes. Collectively, these results demonstrate that the loss of TIEG results in a major perturbation in normal TGFβ-dependent gene expression in OBs with a decrease in the number of genes regulated by TGFβ.

These results demonstrate that TIEG expression in osteoblasts is involved in both osteoblast function and OB support of OC differentiation.

Example 5

TIEG and Hypertrophic Cardiomyopathy

Hypertrophic cardiomyopathy (HCM) is a disease defined by profound genetic and phenotypic heterogeneity (Arad et al., *Human Molecular Genetics* (2002) 11:2499; Maron et al., *New England Journal of Medicine* (1987) 316:780; Maron et al., *New England Journal of Medicine* (1987) 316:844; and Seidman and Seidman, *Cell* (2001) 104:557). Presentation and clinical course range from asymptomatic to severe disability to sudden cardiac death most commonly occurring in the young. Currently, there are over 200 mutations in 10 sarcomeric genes reported for this autosomal dominant disease (Vikstrom and Leinwand, *Current Opinion in Cell Biology* (1996) 8:97).

Transgenic models exist that overexpress mutant myosin heavy chains (Vikstrom et al., *Zeitschrift fur Kardiologie* (1995) 84:49 and Marian et al., *Journal of Clinical Investigation* (1999) 104:1683), mutant cardiac troponin T (Oberst et al., *Journal of Clinical Investigation* 102:1498 and Tardiff et al., *Journal of Clinical Investigation* (1998) 101:2800), mutant myosin binding protein-C (Yang et al., *Journal of Clinical Investigation* (1998) 102:1292), or cardiac troponin-I (James et al., *Circulation Research* (2000) 87:805) and the myosin (Arg4O3Gln) mutation produced by homologous recombination (Geisterfer-Lowrance et al., *Science* (1996) 272:731). Transgenic and knockout mouse models involving signaling pathways for stress induced hypertrophy include calcineurin (Molkentin et al., *Cell* (1998) 93:215), modulatory calcineurin-interacting protein (MCIP) 1 (Vega et al., *Proc. Natl. Acad. Sci. USA* (2003) 100:669), class II histone deacetylases (HDACs; Zhang et al., *Molec. Cell. Biol.* (2002) 22:7302), homeobox only protein (HOP; Kook et al., *Journal of Clinical Investigation* (2003) 112:863), and MEF2 (Lin et al., *Science* (1997) 276:1404). These important animal models partially recapitulate the classic triad of human HCM: asymmetric septal hypertrophy, myocyte disarray, and fibrosis. Further, these animal models suggest that aberrant activation of calcium-dependent intracellular signaling systems and reprogramming of cardiomyocyte gene expression may represent a final common pathway underlying maladaptive hypertrophy. However, the fundamental cellular mechanisms are not fully known and additional hypertrophic signaling cascades likely exist.

To assess the role of TIEG in cardiac hypertrophy, a cohort of unrelated patients with HCM were screened for TIEG mutations. In addition, a possible functional role of TIEG in the pathogenesis of HCM was examined using TIEG −/− mice.

Methods and Materials

Mutational Analysis of TIEG1 in HCM Cohort: Informed written consent was obtained. 389 unrelated individuals (age 42.5±18.9 years, 215 males) were evaluated and provided a blood sample for molecular genetic testing. Each of these subjects met the clinical diagnostic criteria for HCM: left ventricular wall thickness (LVWT)>13 mm in the absence of another confounding diagnosis. Purgene® DNA extraction kits (Gentra, Inc., Minneapolis, Minn.) were used to extract genomic DNA from peripheral blood lymphocytes. Primers were used to amplify the four polypeptide-encoding exons of TIEG from genomic DNA by the polymerase chain reaction. Sequence variations were detected by denaturing high performance liquid chromatography (DHPLC) (WAVE™, Transgenomic, Omaha, Nev.; Pei and Melmed, *Molecular Endocrinology* (1997) 11:433). For samples with an abnormal DHPLC elution profile, the precise sequence anomaly was determined by automated dye terminator cycle-sequencing using an ABI Prism 377 (Ramos-Morales et al., *Oncogene* (2000) 19:403).

Generation and Analysis of TIEG −/− Mice: Mice lacking the TIEG gene were generated as described herein.

Echocardiography: Before sacrificing the TIEG −/− mice, epicardial imaging was performed using M-mode ultrasound imaging from parasternal short axis views. All imaging was performed using a Vivid FiVe ultra-sound machine and a 15 MHz multi-frequency phased array probe (GE Vingmed, Horten, Norway). Anterior wall thickness was also measured (Echopac version 6.25b software, GE Vingmed, Horten, Norway).

Invasive Hemodynamics: Under ketamine-xylazine anesthestic, right carotid cutdown was performed. Through this arteriotomy, a micromanometer tip pressure catheter (Millar Instruments, Houston, Tex.) was introduced into the left ventricle. The left ventricular pressure recordings were obtained for 20 seconds each and traces were generated.

Experimental Animal Model: Experimental studies were performed evaluating control mice (TIEG +/+) and TIEG −/− mice. The mice were studied from age 4 to 18 months (N=20) for each group. The mice were weighed, and an echocardiogram and hemodynamics were performed before sacrifice. Then, the mice were euthanized by $CO_2$. Immediately after dissection, the hearts were weighed. The ventricles were fixed in formalin and embedded in paraffin. Paraffin embedded sections (6 μm) were cut and stained with Masson Trichrome stain for histopathologic examination. Longitudinal sections taken from the heart in systole at the time of sacrifice were placed in Trump's fixative and analyzed for transmission electron microscopy.

Gene MicroArray: Total RNA was isolated using Trizol Reagent (Invitrogen), and 4 micrograms of RNA was used in microarray analysis on the mouse MOE430A microarray (Affymetrix, Santa Clara, Calif.) containing oligonucleotide probes for approximately 23,000 mouse sequences. Analysis of the gene expression profiles was performed using the GeneSpring 6.1 software (Silicon Genetics, Redwood City, Calif.). Only those genes differentially expressed >2- fold were considered in the analysis.

Reverse Transcriptase Polymerase Chain Reaction: The left ventricles from the 14 to 18 month old mice hearts were frozen immediately for RNA extraction. Total RNA was isolated using the Trizol kit (Introgen). Reverse transcriptase polymerase chain reaction (RT-PCR) analysis was performed for the expression of TIEG (Kook et al., *Journal of Clinical Investigation* (2003) 112:863 and Subramaniam et al., *Nucleic Acids Research* (1995) 23:4907), HOP (Kook et al., *Journal of Clinical Investigation* (2003) 112:863), MEF2 (Lin et al., *Science* (1997) 276:1404), HDACII (Kakar, *Gene* (1999) 240:317), ANF (Zhou and Olson, *Molecular & Cellular Biology* (1994) 14:6232), BNP (Heaney and Melmed, *Best Practice & Research Clinical Endocrinology & Metabolism* (1999) 13:367), and Pttg1 (Pei, *Journal of Biological Chemistry* (1998) 273:5219). GAPDH expression was tested as a control.

Immunohistochemistry of Mouse and Human Cardiac Tissues: Immuno-staining of the human myectomy specimens and mouse ventricles was performed to identify Pttg1 (Santa Cruz, Calif.). After fixation, slides were treated sequentially with 3.0% (v/v) $H_2O_2$ for 15 minutes and normal mouse serum for 20 minutes, washed with phosphate buffered saline (w/v) (PBS) for 10 minutes, and incubated in 1:50 anti-Pttg1 for 16 hours at 4° C. To develop color, slides were incubated in 3-amino-9-ethylcarbazole (Sigma Chemical Co., St. Louis, Mo.) and washed with $H_2O$ for 5 minutes.

Results

Mutational analysis of TIEG revealed a non-synonymous single nucleotide polymorphism (amino acid variant) in one patient involving a substitution of isoleucine (I) with methionine (M) at residue 470 (I470M). This variant was absent in 400 reference alleles. However, due to unavailability of DNA from first degree relatives, a co-segregation analysis could not be performed to further implicate this specific TIEG variant as a HCM-associated mutation. To further delineate a potential role of TIEG in HCM, a TIEG knockout mouse was generated and found to recapitulate fully the triad of human HCM: unexplained hypertrophy, myocyte disarray, and fibrosis. In addition, microarray analysis of heart tissue-derived mRNA from 18 month old TIEG −/− mice revealed a striking 13.81-fold upregulation in Pttg1. The presence of Pttg1 was confirmed in tissue specimens from patients who underwent a surgical myectomy for their HCM.

Cardiac Hypertrophy in the TIEG −/− mice: All parameters of the TIEG −/− mice hearts were compared to the wild type control mice. An initial observation was hypertrophy in the 18-month-old TIEG −/− mice. The finding of a striking (214%) increase in cardiac mass was confirmed by the heart weight/body weight ratio TIEG −/− (0.944±0.12) versus control (0.44±0.17). A photograph of the longitudinal cross section of the TIEG +/+ mice versus TIEG −/− mice demonstrated the septal wall abnormality. The anterior wall septal thickness was measured by m-mode, and an increase was found in the TIEG −/− 18-month-old mice. The anterior wall measured 1.67±0.35 mm compared to wild type (1.13±0.15, $p<0.04$). The TIEG −/− mice developed left ventricular cavity obliteration and an increase in wall thickness at 18 months. The left ventricular pressure tracings for the TIEG +/+ mice versus TIEG −/− mice were then compared. There was no statistical difference in the systolic blood pressures measured in both mouse lines.

Masson Trichrome and Electron Microscopy of the TIEG mice: Low magnification histologic analysis of the experimental TIEG −/− mice was compared to that of wild-type mice at age 18 months. A masson trichrome stain demonstrated large areas of fibrosis present in the TIEG −/− left ventricle as compared to the wild-type control. An oil immersion, higher magnification of the masson trichrome stain revealed the myocyte disarray in the TIEG −/− mice as compared to wild-type mice. Myocyte hypertrophy and disarray as well as fibrosis were universal findings in each 18-month-old TIEG −/− mouse studied. Transmission electron microscopy revealed that the TIEG −/− mice had a significantly abnormal sarcomeric architecture and myofibrillar disarray.

Gene Array and RT-PCR: RT-PCR was performed for the known stress induced hypertrophy genes. There were no differences in the gene expression for HOP, MEF, HDAC, ANF, and BNP in the TIEG −/− mice as compared to the results from wild-type mice. As expected, TIEG mRNA was absent in the knockout mice at 18 months. The gene microarray analysis revealed an increase in the expression levels of several genes (Table 1).

TABLE 1

Microarray results.

| Fold Change | Name | Accession # | Description |
|---|---|---|---|
| 13.81 | Pttg 1 | AF069051 | Pituitary tumor-transforming 1 |
| 5.66 | My 17 | NM_002879 | Myosin light polyypeptide 7, regulatory 10 |
| 3.56 | 1500035H01 | NM_023831 | RIKEN cDNA 1500035HO1 |
| 3.41 | Wifl | BC004048 | Wnt Inhibitory factor 1 |
| 3.03 | Anxa8 | NM_013473 | Annexin A8 |

Pituitary tumor-transforming 1 (Pttg1) was increased 13.8 fold in the TIEG −/− mice. The gene expression of Pttg1 was confirmed in the myocardium, and an increase in Pttg1 in the TIEG −/− aged mice was detected as compared to the control. In addition, there is marked increase in protein levels of Pttg1 in the TIEG −/− mice as compared to the TIEG +/+ mice at age 18 months. Further, positive Pttg1 protein expression was confirmed in surgical myectomy tissue derived from patients with HCM.

Masson Trichrome of the Mice and the Human Surgical HCM Specimens: The immunohistochemistry and, masson trichrome of hearts from mice at age 4, 8, 12, and 18 months were compared to heart tissue from patients with HCM. Beginning at about 8 months of age, the TIEG −/− mice start to develop interstitial fibrosis as indicated by blue staining areas. This stain increases dramatically in the TIEG −/− mice as the mice age to 18 months. The presence of blue staining fibrosis in the aged mice is similar to the human HCM specimens.

These results demonstrate an involvement of TIEG in the pathogenesis of HCM. In addition, the results presented herein demonstrate that a TIEG null animal fully develops the phenotype of human HCM. For example, TIEG knock out mice fully recapitulate the phenotype of human HCM with the development of late onset, severe cardiac hypertrophy (in the absence of hypertension) accompanied by myofibrillar disarray and fibrosis. Thus, the non-human animals provided herein that lack TIEG polypeptide expression can be used as non-stress induced models to study heart conditions such as HCM.

The results provided herein also demonstrate that Pttg1 polypeptides (also known as securing polypeptides) can mediate hypertrophic responses. For example, the gene array results provided herein revealed an upregulation of Pttg1 mRNA. These results suggest a pathway model whereby TIEG acting as a hypertrophy suppressor signaling molecule normally binds to and down-regulates Pttg1 via binding to Sp1 sites. In the absence of TIEG Pttg1 is dramatically up-regulated, and the hypertrophic process ensues.

Analysis of TIEG knockout mice (TIEG −/− mice) revealed that TIEG −/− mice develop late onset, non-stress induced severe asymmetric (left) ventricular hypertrophy (HCM) which recapitulates human HCM. There was a 100% penetrance of HCM in the adult male with myofibrillar disarray, fibrosis, and myocyte hypertrophy, but 0% penetrance in the adult female. Using gene arrays (transcriptomes), four regulatory genes were found to be significantly altered in the TIEG −/− HCM hearts. The most pronounced (about 14-fold increase) and relevant alteration was the increase in PTTG-1 expression. PTTG-1 is a potent oncogene that is expressed in many cell types, including heart cells, and is an inducer of cell proliferation, cell hypertrophy, and aneuploidy. It regulates the expression/activity of proto-oncogenes, tumor suppressor genes, and growth factors. One hypothesis is that the inhibition of TIEG expression blocks the TGFβ/BMP signaling pathway and results in a marked increase in pttg-1 and other gene expressions (e.g., α-myosin light chain regulatory protein), loss of cell cycle control, and the development of a severe pattern of late onset asymmetric HCM. Defects in TIEG-1 (or pttg-1) gene expressions may be responsible for the development of HCM in a subset of the human population with this disease.

Example 6

Assessing the Involvement of TIEC Sex Hormones, and PTTG-1 in HCM

The following experiments can be performed to assess the involvement of TIEG, sex hormones, and PTTG-1 in HCM.

The phenotypes of the 4 month old (early stage HCM) and 16 month old (advanced stage HCM) TIEG −/−, TIEG ±, and TIEG +/+ male mouse hearts are characterized and compared to assess the penetrance of the TIEG knockout. This includes assessing histology, cardiac MR1, echocardiography, catheter hemodynamics, electrocardiographic monitoring, cell hyperplasia and hypertrophy, and the effects of exercise on the early onset of the disease. The molecular phenotypes are compared between the matched age TIEG −/−, TIEG ±, and TIEG +/+ male mouse hearts in terms of incidence/frequency of the disease and its expression of HCM related genes using microarray analysis. In addition, an in vitro myocyte culture model is developed. Briefly, cardiomyocyte cells are isolated from TIEG −/−, TIEG ±, or TIEG +/+ hearts, and the cellular and molecular properties of the isolated cells in culture are compared to those observed in vivo in the TIEG −/−, TIEG ±, and TIEG +/+ male hearts.

A sex steroid dependency of the gender-specific (male) phenotype for HCM is examined with emphasis on, for example, estrogen (E). Using, for example, 14 month old TIEG −/− male and female mouse models, the incidence of HCM in orchiectomized (ORX) TIEG −/− male mice and ovariectomized (OVX) TIEG −/− female mice is compared to that observed in intact male TIEG −/− mice. If ORX male mice fail to develop HCM (i.e., androgen (DHT) dependency of the HCM) or if OVX female mice develop HCM (i.e., E protection against the HCM), then mice can be tested to determine whether (1) the respective steroid hormone replacement or (2) the E treatment of castrated male mice, or the DHT treatment of castrated female mice, will enhance the incidence of the disease.

If a sex hormone encourages (e.g., DHT) or inhibits (e.g., E) the development of HCM, then the global gene expression is compared by gene microarray together with Pathway Assist analysis to identify the involved signaling pathways for the particular steroid which protects/encourages the development of HCM. The in vitro cardiomyocyte culture system described above can be used to determine if cells from female TIEG −/− mice are estrogen responsive.

The actions of four candidate TIEG −/− targets, which show potential function and differences in levels of expression, is examined. These are pttg-1, the regulatory protein for myosin light chain, and the two Wnt pathway members, Wnt factor-1, and Dikkopf homology protein. The pttg-1 is emphasized due to its 14 fold induction in the absence of TIEG in HCM hearts. First, male TIEG (−/−)/pttg (+/+) mice are cross-breed with TIEG (+/+)/pttg (−/−) mice to obtain TIEG (−/−)/pttg (−/−) offspring. The resulting TIEG (−/−)/pttg (−/−) mice are examined to determine if males develop HCM compared to TIEG (−/−)/pttg (+/+) controls. No HCM incidence in the double knockout would support pttg-1 as the major TIEG target gene in HCM development.

If pttg-1 appears to play a role in development of HCM in the male TIEG −/− mice, then transgenic TIEG +/+ (normal) male mice which overexpress pttg-1 in the heart tissues can be developed to determine if these animals develop adult male HCM similar to or at a younger age than do TIEG −/− male mice.

TIEG −/− cardiomyocytes in culture are used to determine whether or not overexpression of TIEG or a reduction in pttg-1 expression will reverse the hypertrophism in these cells as determined, for example, by decreases in cell size and protein synthesis, reverses the changes in gene expression patterns, and/or reductions in the organization of the sarcomere as observed with TIEG −/− myocytes in vivo. In addition, TIEG +/+ cardiomyocytes in culture are used to determine whether or not reduction in TIEG expression or an increase in pttg-1 expression will generate a hypertrophic myocyte. If pttg-1 fails to play a role in the development of HCM, then the role of the regulatory protein for myosin light chain, Wnt factor-1, and Dikkopf homology protein is examined in a similar manner.

Genomic and proteomic techniques are used to elucidate a TIEG/PTTG1 signaling pathway in human HCM. The genomic techniques involve a mutational analysis of TIEG as a candidate gene for human HCM. Comprehensive mutational analysis of polypeptide-encoding exons of TIEG is performed on a cohort of over 500 unrelated patients with unequivocal and unexplained cardiac hypertrophy (e.g., human HCM) using denaturing high performance liquid chromatography and direct DNA sequencing. Non-synonymous TIEG variants are characterized functionally using a Smad 7 Promoter assay. The proteomic techniques involve exploration of the relationship between TIEG and PTTG1 at a transcriptional as well as polypeptide level in human myectomy specimens from patients with unequivocal HCM who underwent surgical removal of hypertrophied and obstructive myocardium to alleviate the refractory symptoms. The levels of TIEG and Pttg1 mRNA and polypeptide expression is measured in fresh frozen myocardial tissue from 32 HCM patients who received palliative myectomy.

Example 7

Effect of TIEG on Mechanical Properties of Tail Tendon

Fascicles from the tail tendons of twelve-week old male and female control (n=5) and TIEG knockout (n=5) mice were tested to compare mechanical properties. Using a micro-mechanical tester, the tendons were subjected to three loading scenarios: ramp test, stress relaxation test, and stretch-release cyclical test. The tail tendon cross sections were also measured using optical and transmission electronic microscopy.

The control group exhibited higher (about 10%) dynamic and relaxed forces compared to those exhibited in TIEG −/− mice. In addition, the tendon strength stress was also higher (about 30%) for the control group. These results demonstrate that TIEG −/− mice (aged of 12 weeks) exhibit lower mechanical properties than the control group.

The morphological analysis revealed the presence of more connective tissue in TIEG −/− mice. In addition, the size of the collagen bundle was smaller in TIEG −/− mice when compared to the size observed in control mice. These morphological differences between control and TIEG −/− groups can explain the lower mechanical properties exhibited in TIEG −/− mice.

Example 8

Wound Healing Properties of TIEG −/− Mice

While overall growth and development are remarkably normal in TIEG −/− mice, the effect of the TIEG −/− state, and the resulting interference with normal TGF-β pathways, on wound healing has not been studied. The following is performed to study the course of wound healing in a TIEG −/− mouse model as compared to normal mice. Wild-type and TIEG −/− mice undergo incision and repair at day 0. The mice are further divided into groups varied on the allowed healing time (time=3, 7, and 14 days). The mice are sacrificed, and skin samples, which include the healing wound, are harvested for tensile property and histologic analysis. The disruption of the TGF-β pathway by knocking out TIEG expression can result in an altered healing pattern.

Example 9

The Effect of TIEG on the Contraction of Fibroblast-Seeded Collagen Gels

The process of tendon healing follows a pattern similar to that of other healing tissues. Fibroblasts are seeded in collagen gels and allowed to contract around an inner ring. The fibroblasts are obtained from skin and tendon samples from both TIEG −/− and wild-type mice. After gel contraction, the rings are subjected to mechanical testing and analyzed histologically. Performing this experiment can allow investigation of the role of TIEG in fibroblast function.

Example 10

Effect of TIEG on PTTG Promoter Activity

Figure 14:
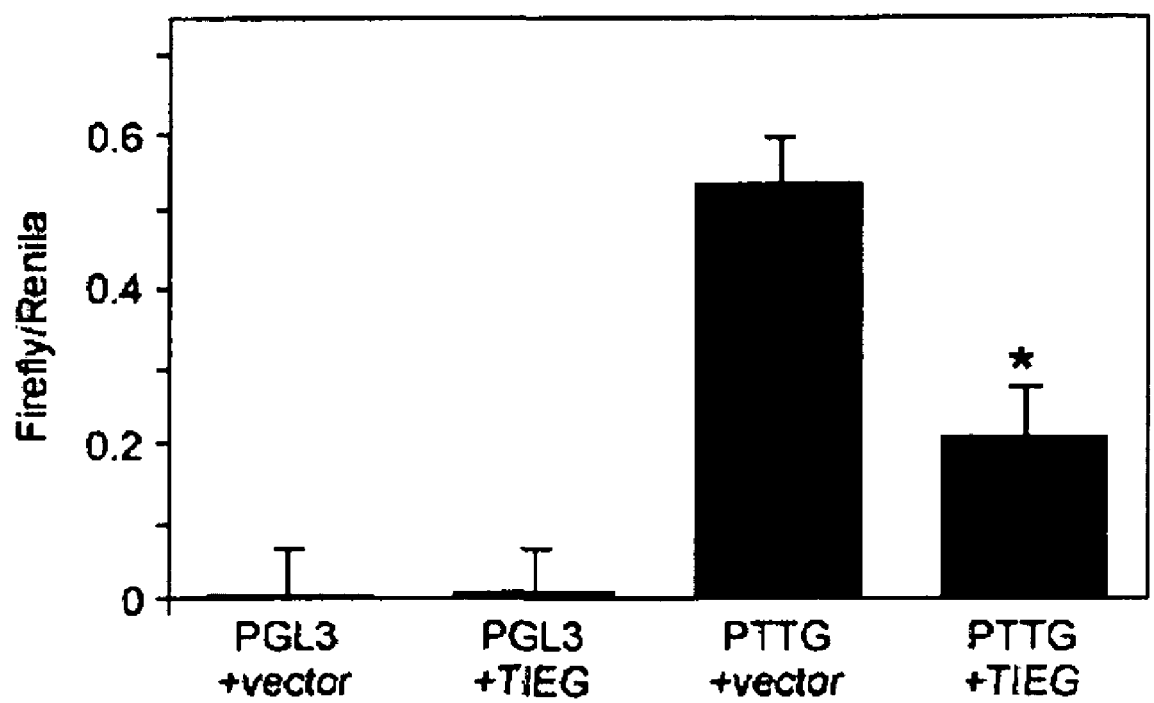
FIG. 14 is a bar graph plotting duel luciferase activity for AKR2B mouse embryo fibroblasts containing the indicated PTTG promoter or pGL3 basic luciferase construct (1 µg) with either an empty expression vector (1 µg) or a vector driving TIEG polypeptide expression (1 µg). As an internal control for transfection efficiency, 0.5 µg of renilla luciferase was also transfected into the cells. The cells were analyzed 24 hours after transfection.

The results obtained from gene array analysis comparing the gene expression profiles of TIEG +/+ and TIEG −/− heart tissues revealed that PTTG was highly expressed in TIEG −/− hearts, suggesting that TIEG negatively regulates pttg gene expression. These results were confirmed through RT-PCR analysis. To further determine if the regulation of pttg gene expression by TIEG polypeptide occurs at the promoter level, the pttg promoter containing the 5'-flanking region (−1321 to −3) was cloned in front of a luciferase reporter. This construct was used to perform a transfection analysis. When the pttg promoter construct was transfected into AkR2B mouse embryo fibroblasts, an increased promoter activity was observed as compared to the basic luciferase construct (FIG. 14). When the promoter construct was co-transfected with a TIEG expression vector, a 60-70 percent decrease in the promoter activity was observed. These results demonstrate that TIEG polypeptides can negatively regulate pttg gene expression by possibly binding to the regulatory sequences of a pttg promoter.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse whose genome comprises a disruption of an endogenous transforming growth factor-β-inducible early gene (TIEG) nucleic acid, wherein:
   (a) said mouse is homozygous for said disruption, is a male mouse, and develops cardiac hypertrophy,
   (b) said mouse is homozygous for said disruption and is a female mouse, wherein male progeny of said female mouse that are homozygous for said disruption develop cardiac hypertrophy, or
   (c) said mouse is heterozygous for said disruption, and wherein male progeny of said mouse that are homozygous for said disruption develop cardiac hypertrophy.

2. The transgenic mouse of claim 1, wherein the genetic background of said mouse is selected from the group consisting of B6, 129Sv/J, and FVB.

3. The transgenic mouse of claim 1, wherein said mouse is a male mouse and is homozygous for said disruption.

4. The transgenic mouse of claim 3, wherein said mouse exhibits a symptom of human hypertrophic cardiomyopathy.

5. The transgenic mouse of claim 1, wherein said disruption results from deletion of a portion of the endogenous TIEG gene.

6. The transgenic mouse of claim 5, wherein exons 1 and 2 of said endogenous TIEG are deleted.

7. Progeny of the transgenic mouse of claim 1, wherein said progeny comprise a disruption of an endogenous TIEG gene.

8. Cells isolated from the transgenic mouse of claim 1.

9. The cells of claim 8, wherein said cells are cardiomyocytes, osteoblasts, or osteoclasts.

* * * * *

UNITED STATES PATENT AND TRADEMARK OFFICE
CERTIFICATE OF CORRECTION

| | | |
|---|---|---|
| PATENT NO. | : 7,304,203 B2 | Page 1 of 1 |
| APPLICATION NO. | : 10/944454 | |
| DATED | : December 4, 2007 | |
| INVENTOR(S) | : Thomas C. Spelsberg | |

It is certified that error appears in the above-identified patent and that said Letters Patent is hereby corrected as shown below:

Title Page, Item (56) References Cited, Other Publications, Fautsch et al. reference, please delete "Oct. 9, 1998(10)838-42" and insert --1998, Oct., 9(10):838-42-- therefor;

Title Page (Page 2), Item 56 References Cited, Other Publications, Hyrup and Nielssen reference, please delete "Nielssen" and insert --Nielsen-- therefor;

Title Page (Page 2), Item (56) References Cited, Other Publications, Noti et al. reference, please delete "CDIId" and insert --CDlld-- therefor.

Signed and Sealed this

Twenty-third Day of September, 2008

JON W. DUDAS
*Director of the United States Patent and Trademark Office*

SEQUENCE LISTING

```
<160> NUMBER OF SEQ ID NOS: 37

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide

<400> SEQUENCE: 1
aagacctgca ataatccaga a                                              21

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2
aatggctact ctgatctatg t                                              21

<210> SEQ ID NO 3
<211> LENGTH: 21
<212> TYPE: DNA
```

```
<213> ORGANISM: Artificial Sequence
<220> FEATURE:
<223> OTHER INFORMATION: Oligonucleotide

<400> SEQUENCE: 3
aaagccttag atgggagatc t                                              21

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide

<400> SEQUENCE: 4
aaaggctttg ggaactgtca a                                              21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
aagatgactg agaagactgt t                                              21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
aatctgttgc agtctccttc a                                              21

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide

<400> SEQUENCE: 7
aagctctgtt cctgcctcag a                                              21

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide

<400> SEQUENCE: 8
gaatagcctc tccacccaag cgg                                            23

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
cctctaattc ctctccttgc                                                20
```

```
<210> SEQ ID NO 10
<211> LENGTH: 28
<212> TYPE: DNA
<213> ORGANISM: Artificial Sequence
<220> FEATURE:
<223> OTHER INFORMATION: Oligonucleotide

<400> SEQUENCE: 10
tggtggttgc acagttgggc atcagctg                                          28

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide

<400> SEQUENCE: 11
acgcgcaccg cgtgcctcct gct                                               23

<210> SEQ ID NO 12
<211> LENGTH: 32
<212> TYPE: DNA
<213> ORGANISM: Artificial Sequence
<220> FEATURE:
<223> OTHER INFORMATION: Oligonucleotide

<400> SEQUENCE: 12
ctaaggtgat gggggttgca gcacaccagc tc                                     32

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
caccatggag aaggccgggg                                                   20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
gacggacaca ttgggggtag                                                   20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
gtctcagtgc tcccgtctgt                                                   20

<210> SEQ ID NO 16
<211> LENGTH: 20
<212> TYPE: DNA
<213> ORGANISM: Artificial Sequence
<220> FEATURE:
```

<223> OTHER INFORMATION: Oligonucleotide

<400> SEQUENCE: 16
ccaccgcttc aaagtcactc                                                     20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
tctcaactgt tctagttcct                                                     20

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide

<400> SEQUENCE: 18
ttgggtcatt tccacatgc                                                      19

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
tctccactct tctagttcct                                                     20

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide

<400> SEQUENCE: 20
ttgggtcatt tccacatgc                                                      19

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide

<400> SEQUENCE: 21
tgaggaagaa gcccattcac                                                     20

<210> SEQ ID NO 22
<211> LENGTH: 19
<212> TYPE: DNA
<213> ORGANISM: Artificial Sequence
<220> FEATURE:
<223> OTHER INFORMATION: Oligonucleotide

<400> SEQUENCE: 22
acttcttctc ccgggtgtg                                                      19

```
<210> SEQ ID NO 23
<211> LENGTH: 20
<212> TYPE: DNA
<213> ORGANISM: Artificial Sequence
<220> FEATURE:
<223> OTHER INFORMATION: Oligonucleotide

<400> SEQUENCE: 23
tctgacaaac cttcatgtcc                                                   20

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide

<400> SEQUENCE: 24
aaatagtgat accgtagatg cg                                                22

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
caccatggag aaggccgggg                                                   20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide

<400> SEQUENCE: 26
gacggacaca ttgggggtag                                                   20

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide

<400> SEQUENCE: 27
ctaaagcgca tgctccagac tgcc                                              24

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide

<400> SEQUENCE: 28
cctctaattc ctctccttgc                                                   20

<210> SEQ ID NO 29
<211> LENGTH: 28
<212> TYPE: DNA
<213> ORGANISM: Artificial Sequence
<220> FEATURE:
<223> OTHER INFORMATION: Oligonucleotide
```

<400> SEQUENCE: 29
tggtggttgc acagttgggc atcagctg                              28

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
ctctggctgg cttggcttgg                                       20

<210> SEQ ID NO 31
<211> LENGTH: 19
<212> TYPE: DNA
<213> ORGANISM: Artificial Sequence
<220> FEATURE:
<223> OTHER INFORMATION: Oligonucleotide

<400> SEQUENCE: 31
gcagaaggat gaggttgtg                                        19

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide

<400> SEQUENCE: 32
acggacagct ggcacaccag                                       20

<210> SEQ ID NO 33
<211> LENGTH: 17
<212> TYPE: DNA
<213> ORGANISM: Artificial Sequence
<220> FEATURE:
<223> OTHER INFORMATION: Oligonucleotide

<400> SEQUENCE: 33
acacactcgg ttgtggg                                          17

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide

<400> SEQUENCE: 34
ggaggaccat gaaccctttc c                                     21

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide

<400> SEQUENCE: 35
gctggctgct gcttcactgg                                       20

<210> SEQ ID NO 36
<211> LENGTH: 22

```
<212> TYPE: DNA
<213> ORGANISM: Artificial Sequence
<220> FEATURE:
<223> OTHER INFORMATION: Oligonucleotide

<400> SEQUENCE: 36
ctgctcatca gcaagatcag ag                                              22

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide

<400> SEQUENCE: 37
gcattatagg gtccaccaca g                                               21
```